United States Patent [19]
Chandler

[11] Patent Number: 5,846,838
[45] Date of Patent: Dec. 8, 1998

[54] OPPOSABLE-ELEMENT ASSAY DEVICE EMPLOYING CONDUCTIVE BARRIER

[75] Inventor: Howard M. Chandler, Yarmouth, Me.

[73] Assignee: SmithKline Diagnostics, Inc., Palo Alto, Calif.

[21] Appl. No.: 879,693

[22] Filed: Jun. 18, 1997

Related U.S. Application Data

[60] Division of Ser. No. 458,132, Jun. 2, 1995, which is a continuation-in-part of Ser. No. 40,430, Mar. 31, 1993, abandoned, which is a continuation-in-part of Ser. No. 888,831, May 27, 1992, abandoned, which is a continuation-in-part of Ser. No. 706,639, May 29, 1991, abandoned.

[51] Int. Cl.$^6$ ..................... G01N 33/558; G01N 33/543
[52] U.S. Cl. ..................... 436/514; 422/55; 422/56; 422/57; 422/58; 435/287.1; 435/287.2; 435/287.7; 435/287.8; 435/287.9; 435/805; 435/810; 435/970; 435/973; 435/975; 436/169; 436/518; 436/530; 436/805; 436/808; 436/810
[58] Field of Search ..................... 422/55–58; 435/287.1, 435/287.2, 287.7, 287.8, 287.9, 805, 810, 970, 973, 975; 436/514, 518, 530, 169, 805, 808, 810

[56] References Cited

U.S. PATENT DOCUMENTS

| | | |
|---|---|---|
| 3,723,064 | 3/1973 | Liotta . |
| 3,798,004 | 3/1974 | Zerachia et al. . |
| 3,888,629 | 6/1975 | Bagshawe . |
| 3,915,647 | 10/1975 | Wright . |
| 3,933,594 | 1/1976 | Milligan et al. . |
| 3,966,897 | 6/1976 | Renn et al. . |
| 3,985,867 | 10/1976 | Redshaw . |
| 3,990,850 | 11/1976 | Friedman et al. . |
| 3,993,451 | 11/1976 | Verbeck . |
| 3,996,006 | 12/1976 | Pagano . |
| 4,018,662 | 4/1977 | Ruhenstroth-Bauer et al. . |
| 4,094,647 | 6/1978 | Deutsch et al. . |
| 4,108,729 | 8/1978 | Mennen . |
| 4,110,079 | 8/1978 | Schaeffer et al. . |
| 4,168,146 | 9/1979 | Grubb et al. . |
| 4,180,383 | 12/1979 | Johnson . |

(List continued on next page.)

FOREIGN PATENT DOCUMENTS

| | | |
|---|---|---|
| 0068310 | 11/1982 | European Pat. Off. . |
| 0183442 | 6/1986 | European Pat. Off. . |
| 0191640 | 8/1986 | European Pat. Off. . |
| 0225054 | 6/1987 | European Pat. Off. . |
| 0238012 | 9/1987 | European Pat. Off. . |
| 0250137 | 12/1987 | European Pat. Off. . |
| 0262328 | 4/1988 | European Pat. Off. . |
| 0269876 | 6/1988 | European Pat. Off. . |
| 0323605 | 7/1988 | European Pat. Off. . |
| 0277723 A1 | 8/1988 | European Pat. Off. . |
| 0279097 | 8/1988 | European Pat. Off. . |
| 0284232 | 9/1988 | European Pat. Off. . |

(List continued on next page.)

*Primary Examiner*—Christopher L. Chin
*Attorney, Agent, or Firm*—William H. May; P. R. Harder; Merchant & Gould

[57] ABSTRACT

A chromatographic assay device for use with immunoassays allows rapid and convenient assays of analytes of biological interest, and permits extractions to be carried out in situ, avoiding the use of separate extraction vessels. The device has a wide dynamic range and avoids interference from particulates or colored components. In one form, the device comprises: (1) a first opposable component comprising a sample preparation zone adapted to receive a sample to be assayed; (2) a second opposable component comprising a chromatographic medium; and (3) a conductive barrier attached to the second opposable component. The first and second opposable components can be brought into opposition so as to cause the sample preparation zone to apply the sample to be tested to the chromatographic medium. Preferably, the analyte is detected with a visually detectable label. Other variations of the device vary the arrangement of components to provide optimal chromatography for a variety of analytes. The devices can be incorporated in test kits, and assay methods, particularly sandwich immunoassays, using the devices are also disclosed.

6 Claims, 8 Drawing Sheets

U.S. PATENT DOCUMENTS

| | | |
|---|---|---|
| 4,189,304 | 2/1980 | Adams, Jr. et al. . |
| 4,223,089 | 9/1980 | Rothe et al. . |
| 4,246,339 | 1/1981 | Cole et al. . |
| 4,248,965 | 2/1981 | Mochida et al. . |
| 4,279,885 | 7/1981 | Reese et al. . |
| 4,299,916 | 11/1981 | Litman et al. . |
| 4,313,734 | 2/1982 | Leuvering . |
| 4,333,733 | 6/1982 | Sanford et al. . |
| 4,365,970 | 12/1982 | Lawrence et al. . |
| 4,366,241 | 12/1982 | Tom et al. . |
| 4,376,110 | 3/1983 | David et al. . |
| 4,380,580 | 4/1983 | Boguslaski et al. . |
| 4,391,904 | 7/1983 | Litman et al. . |
| 4,411,518 | 10/1983 | Meserol et al. . |
| 4,425,438 | 1/1984 | Bauman et al. . |
| 4,427,769 | 1/1984 | Adlercreutz et al. . |
| 4,435,504 | 3/1984 | Zuk et al. . |
| 4,442,204 | 4/1984 | Greenquist et al. . |
| 4,444,193 | 4/1984 | Fogt et al. . |
| 4,446,232 | 5/1984 | Liotta . |
| 4,447,526 | 5/1984 | Rupchock et al. . |
| 4,447,529 | 5/1984 | Greenquist et al. . |
| 4,459,358 | 7/1984 | Berke . |
| 4,461,829 | 7/1984 | Greenquist . |
| 4,474,878 | 10/1984 | Halbert et al. . |
| 4,477,575 | 10/1984 | Vogel et al. . |
| 4,517,288 | 5/1985 | Giegel et al. . |
| 4,533,629 | 8/1985 | Litman et al. . |
| 4,582,811 | 4/1986 | Pucci et al. . |
| 4,594,327 | 6/1986 | Zuk . |
| 4,623,461 | 11/1986 | Hossom et al. . |
| 4,629,690 | 12/1986 | Weng et al. . |
| 4,642,285 | 2/1987 | Halbert et al. . |
| 4,656,129 | 4/1987 | Wagner . |
| 4,666,866 | 5/1987 | Krauth . |
| 4,668,619 | 5/1987 | Greenquist et al. . |
| 4,678,757 | 7/1987 | Rapkin et al. . |
| 4,683,197 | 7/1987 | Gallati . |
| 4,690,907 | 9/1987 | Hibino et al. . |
| 4,693,834 | 9/1987 | Hossom . |
| 4,703,017 | 10/1987 | Campbell et al. . |
| 4,717,656 | 1/1988 | Swanljung . |
| 4,738,823 | 4/1988 | Engelmann . |
| 4,740,468 | 4/1988 | Weng et al. . |
| 4,752,562 | 6/1988 | Sheiman et al. . |
| 4,757,002 | 7/1988 | Joo . |
| 4,761,381 | 8/1988 | Blatt et al. . |
| 4,775,636 | 10/1988 | Moeremans et al. . |
| 4,780,280 | 10/1988 | Berger et al. . |
| 4,786,594 | 11/1988 | Khanna et al. . |
| 4,789,526 | 12/1988 | Matkovich . |
| 4,789,629 | 12/1988 | Baker et al. . |
| 4,790,979 | 12/1988 | Terminiello et al. . |
| 4,797,260 | 1/1989 | Parker . |
| 4,803,170 | 2/1989 | Stanton et al. . |
| 4,806,311 | 2/1989 | Greenquist . |
| 4,806,312 | 2/1989 | Greenquist . |
| 4,810,470 | 3/1989 | Burkhardt et al. . |
| 4,814,142 | 3/1989 | Gleisner . |
| 4,816,224 | 3/1989 | Vogel et al. . |
| 4,818,677 | 4/1989 | Hay-Kaufman . |
| 4,826,759 | 5/1989 | Guire et al. . |
| 4,837,373 | 6/1989 | Gunkel et al. . |
| 4,837,395 | 6/1989 | Leeder et al. . |
| 4,843,000 | 6/1989 | Litman et al. . |
| 4,851,356 | 7/1989 | Canfield et al. . |
| 4,853,335 | 8/1989 | Olsen et al. . |
| 4,855,240 | 8/1989 | Rosenstein et al. . |
| 4,857,453 | 8/1989 | Ullman et al. . |
| 4,859,612 | 8/1989 | Cole et al. . |
| 4,861,711 | 8/1989 | Friesen et al. . |
| 4,868,108 | 9/1989 | Bahar et al. . |
| 4,876,067 | 10/1989 | Deneke et al. . |
| 4,877,586 | 10/1989 | Devaney, Jr. et al. . |
| 4,879,215 | 11/1989 | Weng et al. . |
| 4,883,764 | 11/1989 | Kloepfer . |
| 4,900,663 | 2/1990 | Wie et al. . |
| 4,904,583 | 2/1990 | Mapes et al. . |
| 4,912,034 | 3/1990 | Kalra et al. . |
| 4,916,056 | 4/1990 | Brown, III et al. . |
| 4,916,078 | 4/1990 | Klose et al. . |
| 4,918,025 | 4/1990 | Grenner . |
| 4,920,045 | 4/1990 | McFarland et al. . |
| 4,938,927 | 7/1990 | Kelton et al. . |
| 4,939,096 | 7/1990 | Tonelli . |
| 4,939,098 | 7/1990 | Suzuki et al. . |
| 4,943,522 | 7/1990 | Eisinger et al. . |
| 4,952,517 | 8/1990 | Bahar . |
| 4,956,275 | 9/1990 | Zuk et al. . |
| 4,956,302 | 9/1990 | Gordon et al. . |
| 4,959,307 | 9/1990 | Olson . |
| 4,960,691 | 10/1990 | Gordon et al. . |
| 4,963,325 | 10/1990 | Lennon et al. . |
| 4,963,468 | 10/1990 | Olson . |
| 4,965,187 | 10/1990 | Tonelli . |
| 4,977,078 | 12/1990 | Niimura et al. . |
| 4,981,786 | 1/1991 | Dafforn et al. . |
| 4,999,285 | 3/1991 | Stiso . |
| 4,999,287 | 3/1991 | Allen et al. . |
| 5,006,464 | 4/1991 | Chu et al. . |
| 5,006,474 | 4/1991 | Horstman et al. . |
| 5,030,555 | 7/1991 | Clemmons . |
| 5,030,558 | 7/1991 | Litman et al. . |
| 5,039,607 | 8/1991 | Skold et al. . |
| 5,051,237 | 9/1991 | Grenner et al. . |
| 5,071,746 | 12/1991 | Wilk et al. . |
| 5,073,484 | 12/1991 | Swanson et al. . |
| 5,075,078 | 12/1991 | Osikowicz et al. . |
| 5,079,142 | 1/1992 | Coleman et al. . |
| 5,079,174 | 1/1992 | Buck et al. . |
| 5,085,987 | 2/1992 | Olson . |
| 5,085,988 | 2/1992 | Olson . |
| 5,096,809 | 3/1992 | Chen et al. . |
| 5,100,619 | 3/1992 | Baker et al. . |
| 5,104,811 | 4/1992 | Berger et al. . |
| 5,104,812 | 4/1992 | Kurn et al. . |
| 5,106,582 | 4/1992 | Baker . |
| 5,106,758 | 4/1992 | Adler et al. . |
| 5,110,550 | 5/1992 | Schlipfenbach . |
| 5,114,673 | 5/1992 | Berger et al. . |
| 5,114,862 | 5/1992 | Brenneman . |
| 5,120,643 | 6/1992 | Ching et al. . |
| 5,120,662 | 6/1992 | Chan et al. . |
| 5,132,208 | 7/1992 | Freitag et al. . |
| 5,135,872 | 8/1992 | Pouletty et al. . |
| 5,135,873 | 8/1992 | Patel et al. . |
| 5,137,804 | 8/1992 | Greene et al. . |
| 5,137,808 | 8/1992 | Ullman et al. . |
| 5,141,850 | 8/1992 | Cole et al. . |
| 5,156,952 | 10/1992 | Litman et al. . |
| 5,158,869 | 10/1992 | Pouletty et al. . |
| 5,160,486 | 11/1992 | Schlipfenbacher et al. . |
| 5,162,237 | 11/1992 | Messenger et al. . |
| 5,164,294 | 11/1992 | Skold et al. . |
| 5,166,078 | 11/1992 | McMahon et al. . |
| 5,177,021 | 1/1993 | Kondo . |
| 5,182,191 | 1/1993 | Fan et al. . |
| 5,185,127 | 2/1993 | Vonk . |
| 5,188,939 | 2/1993 | Mangold et al. . |
| 5,188,966 | 2/1993 | Eikmeier et al. . |
| 5,202,267 | 4/1993 | Ditlow et al. . |
| 5,202,268 | 4/1993 | Kuhn et al. . |

| | | | | | |
|---|---|---|---|---|---|
| 5,209,904 | 5/1993 | Forney et al. . | 0296724 | 12/1988 | European Pat. Off. . |
| 5,223,436 | 6/1993 | Freitag et al. . | 0297292 | 1/1989 | European Pat. Off. . |
| 5,234,813 | 8/1993 | McGeehan et al. . | 0299359 A2 | 1/1989 | European Pat. Off. . |
| 5,248,619 | 9/1993 | Skold et al. . | 0299428 | 1/1989 | European Pat. Off. . |
| 5,256,372 | 10/1993 | Brooks et al. . | 0306772 | 3/1989 | European Pat. Off. . |
| 5,258,163 | 11/1993 | Krause et al. . | 0322340 | 6/1989 | European Pat. Off. . |
| 5,260,193 | 11/1993 | Olson . | WO 89/06799 | 7/1989 | European Pat. Off. . |
| 5,260,222 | 11/1993 | Patel et al. . | 0415679 | 3/1991 | European Pat. Off. . |
| 5,264,180 | 11/1993 | Allen et al. . | 0443231 | 8/1991 | European Pat. Off. . |
| 5,275,785 | 1/1994 | May et al. . | 0516095 | 5/1992 | European Pat. Off. . |
| 5,278,079 | 1/1994 | Gubinski et al. . | 0560410 | 9/1993 | European Pat. Off. . |
| 5,308,580 | 5/1994 | Clark . | 2016687 | 9/1979 | United Kingdom . |
| 5,314,804 | 5/1994 | Boguslaski et al. . | 2204398 | 11/1988 | United Kingdom . |
| 5,415,994 | 5/1995 | Imrich et al. . | WO89/03992 | 5/1989 | WIPO . |
| 5,656,503 | 8/1997 | May et al. . | WO90/05906 | 5/1990 | WIPO . |

FOREIGN PATENT DOCUMENTS

| | | | | | |
|---|---|---|---|---|---|
| | | | WO91/19980 | 12/1991 | WIPO . |
| | | | WO92/01226 | 1/1992 | WIPO . |
| 0291194 | 11/1988 | European Pat. Off. . | WO93/03176 | 2/1993 | WIPO . |

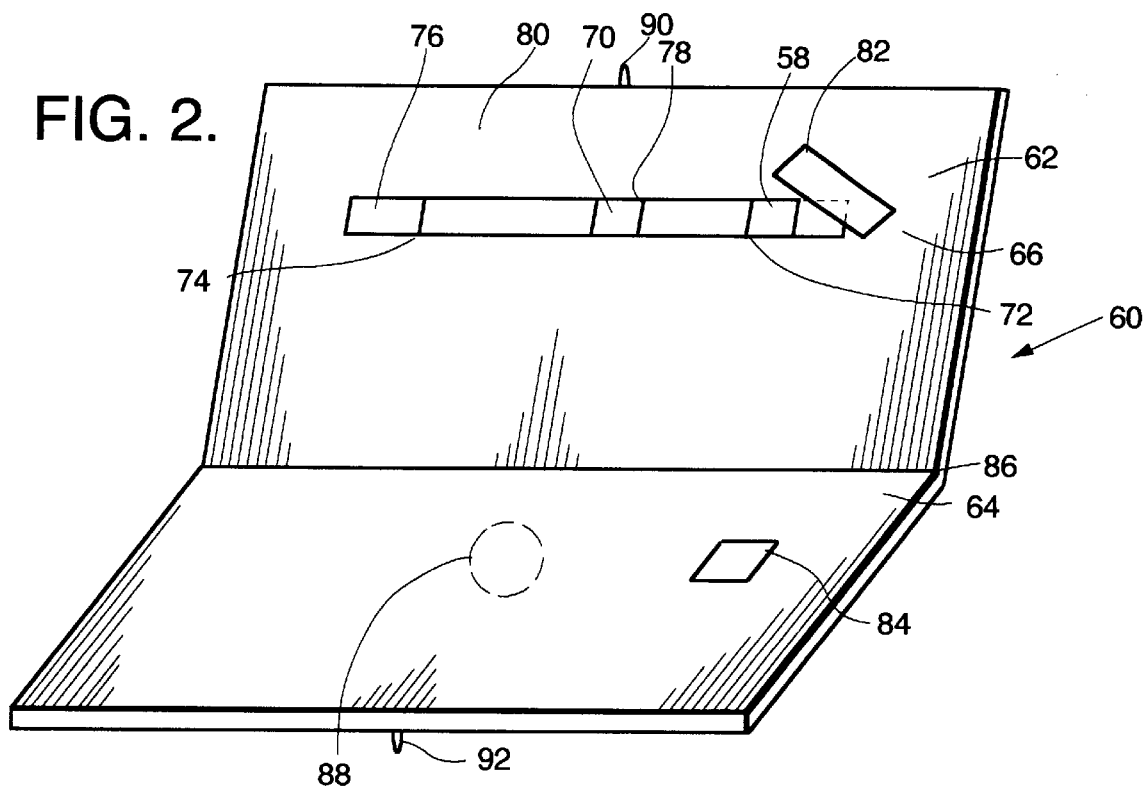
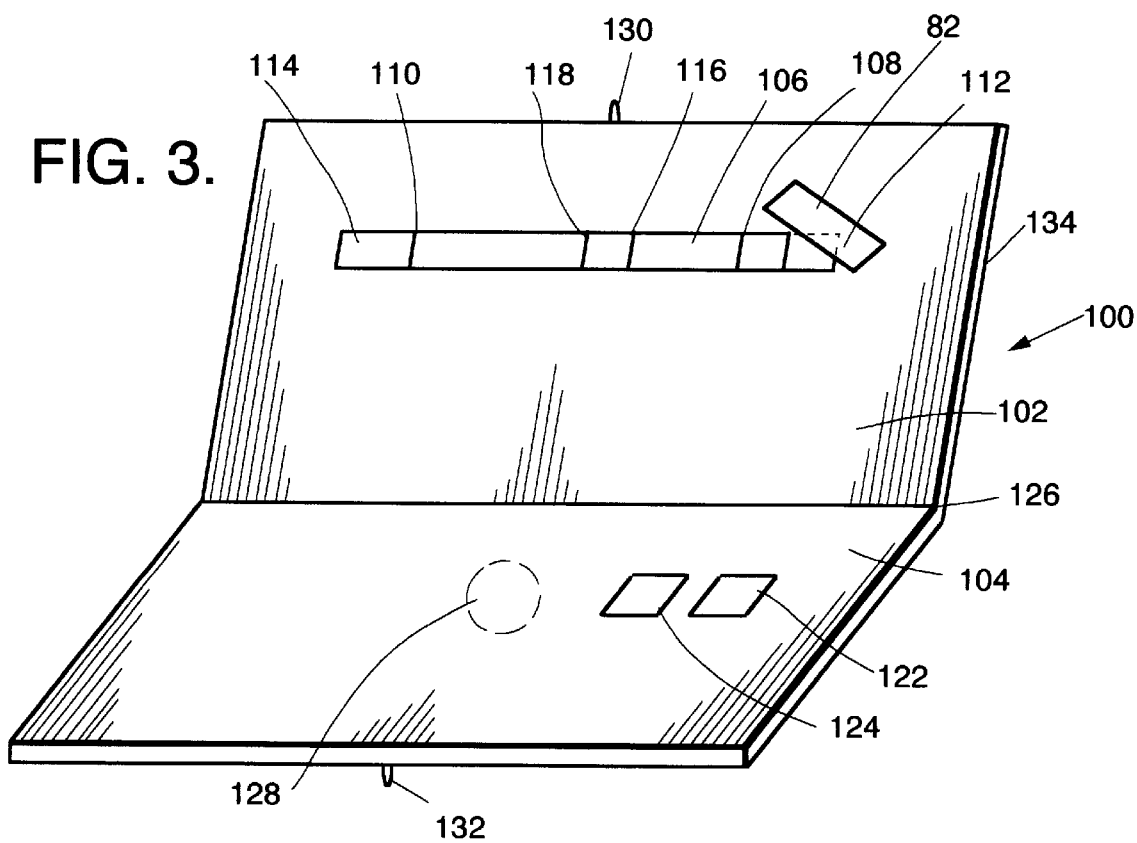

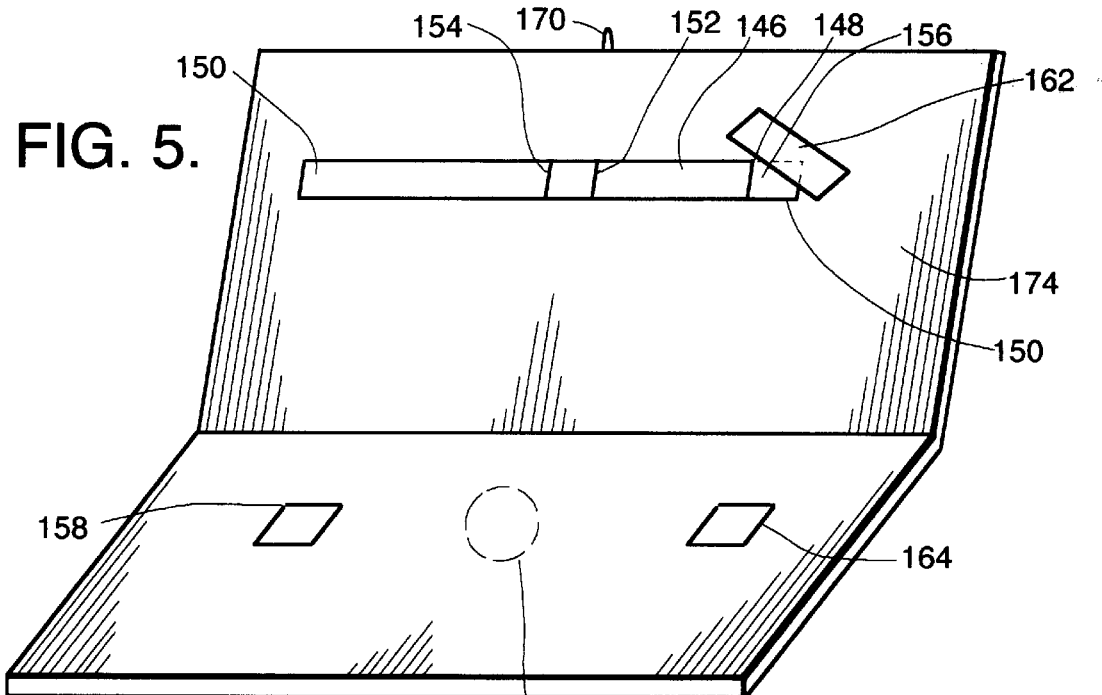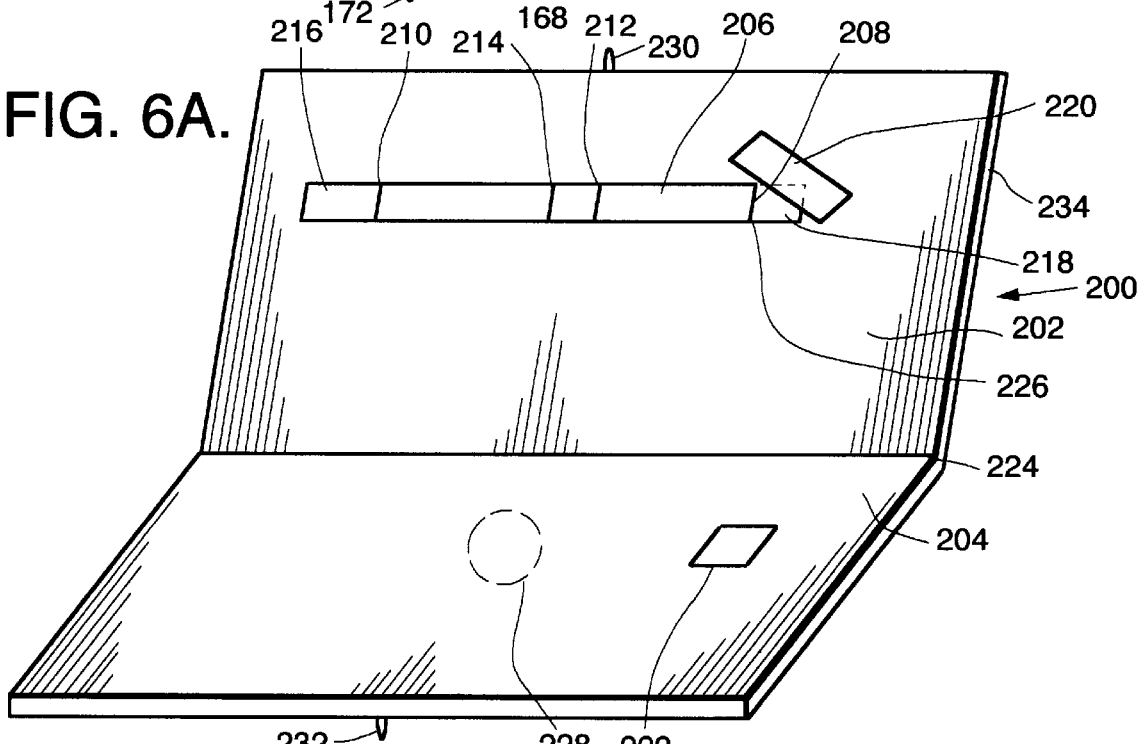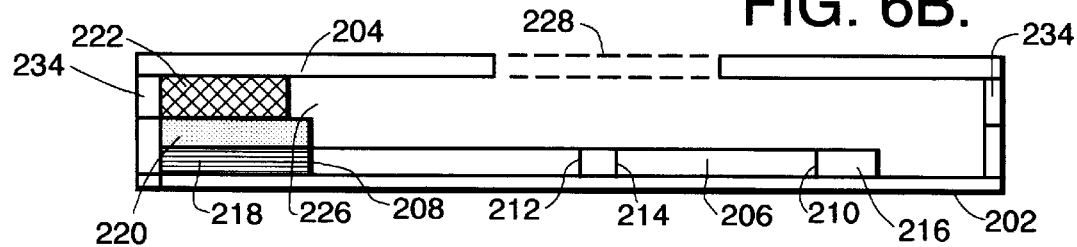

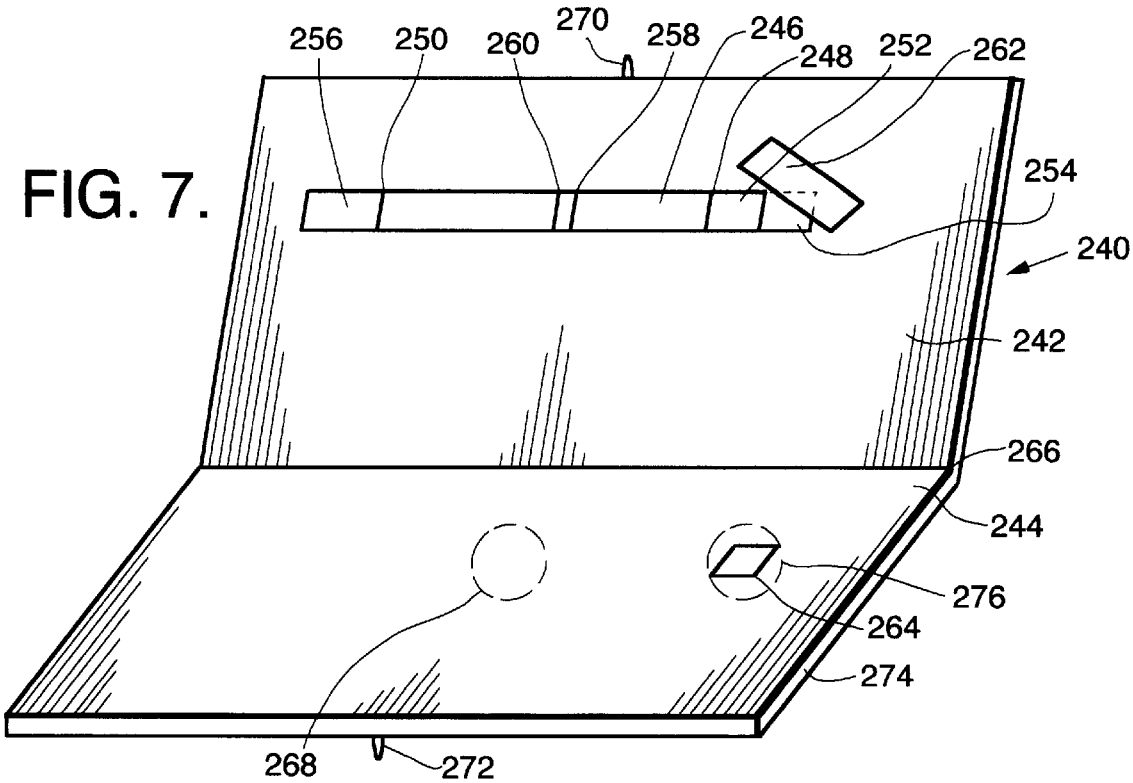
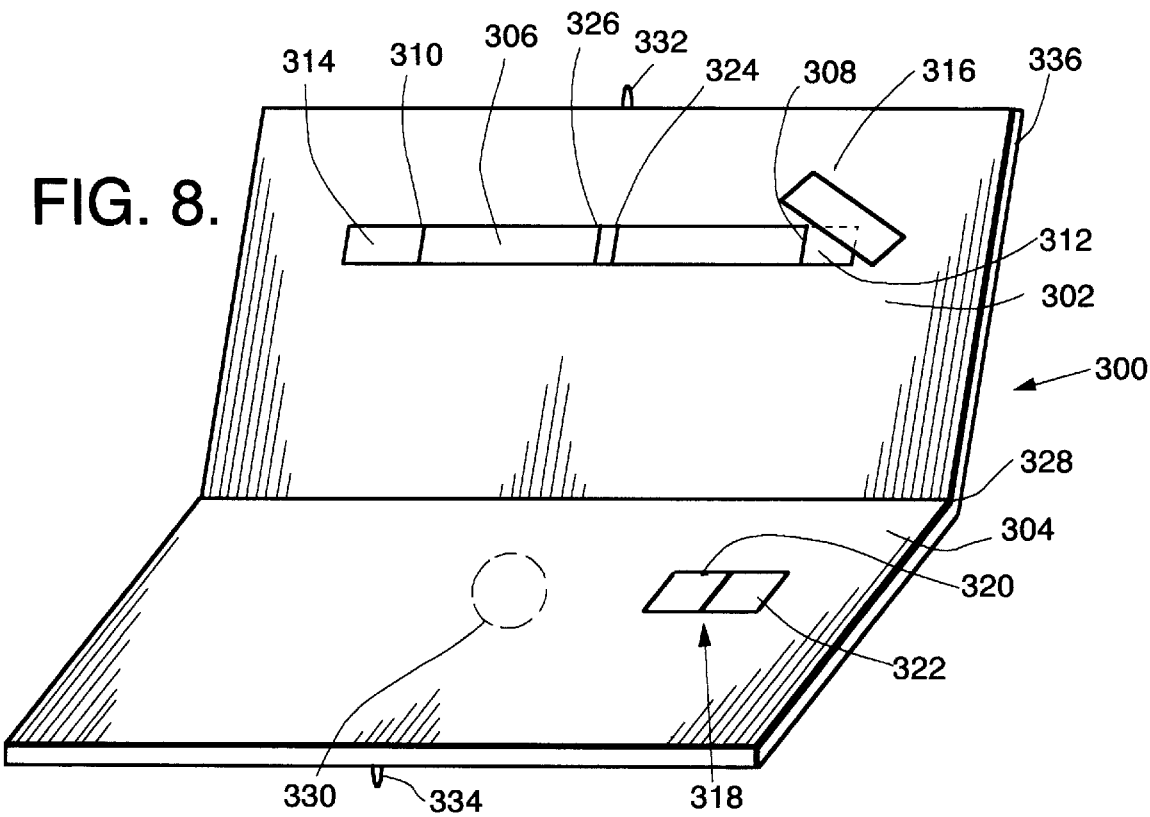

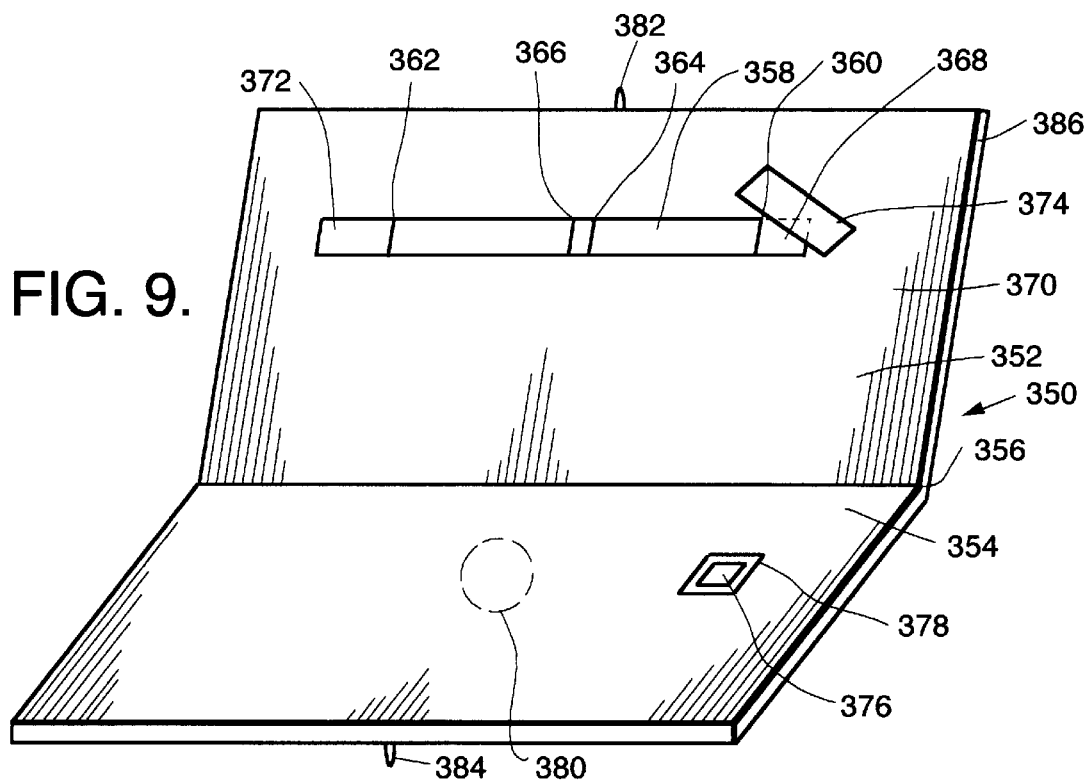
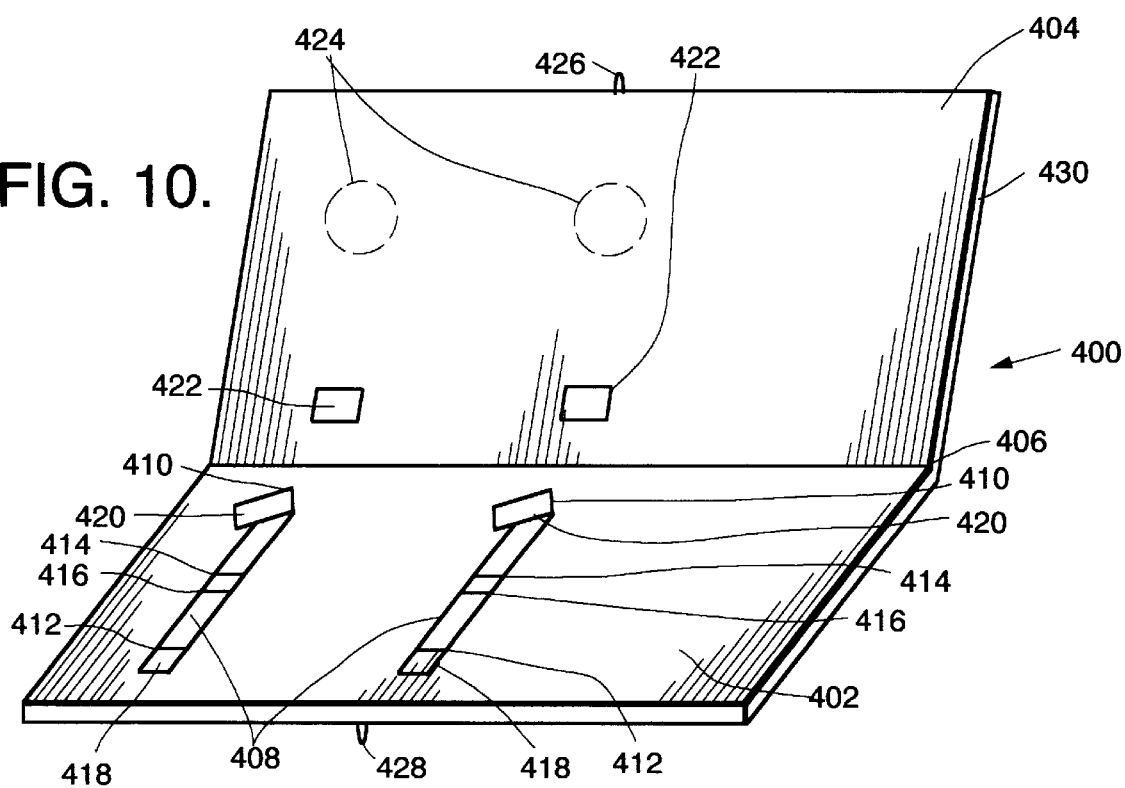

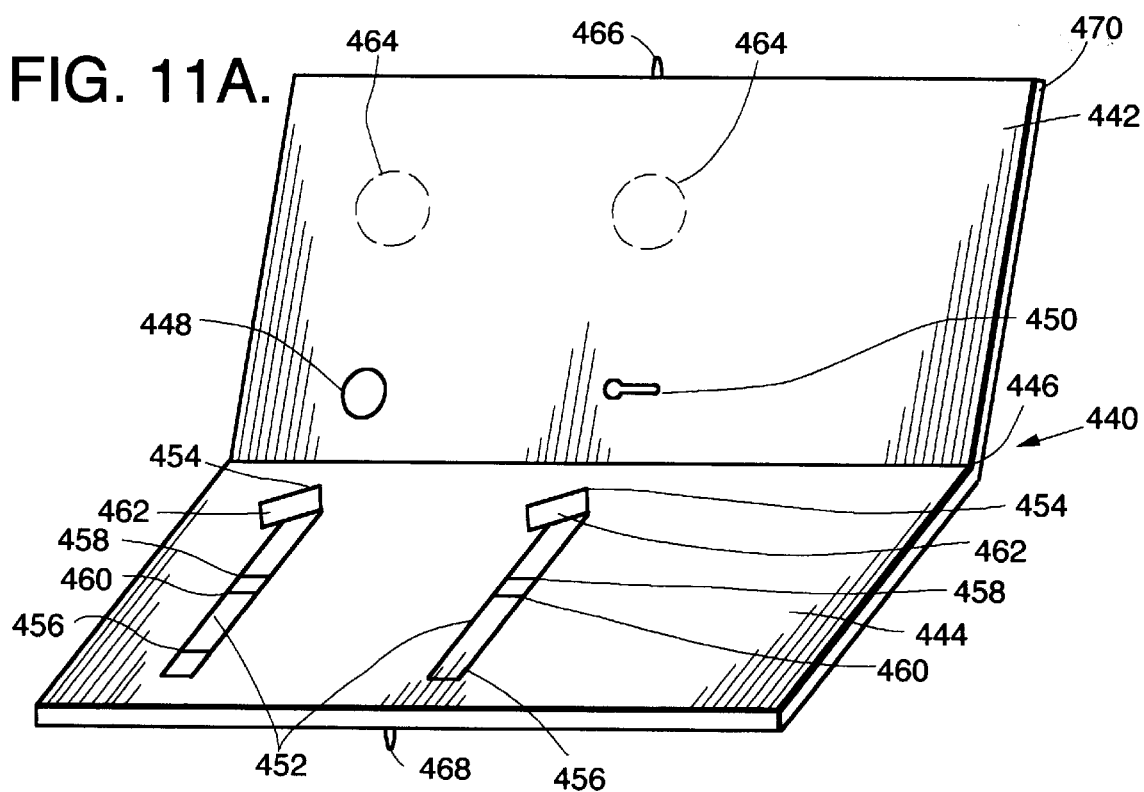
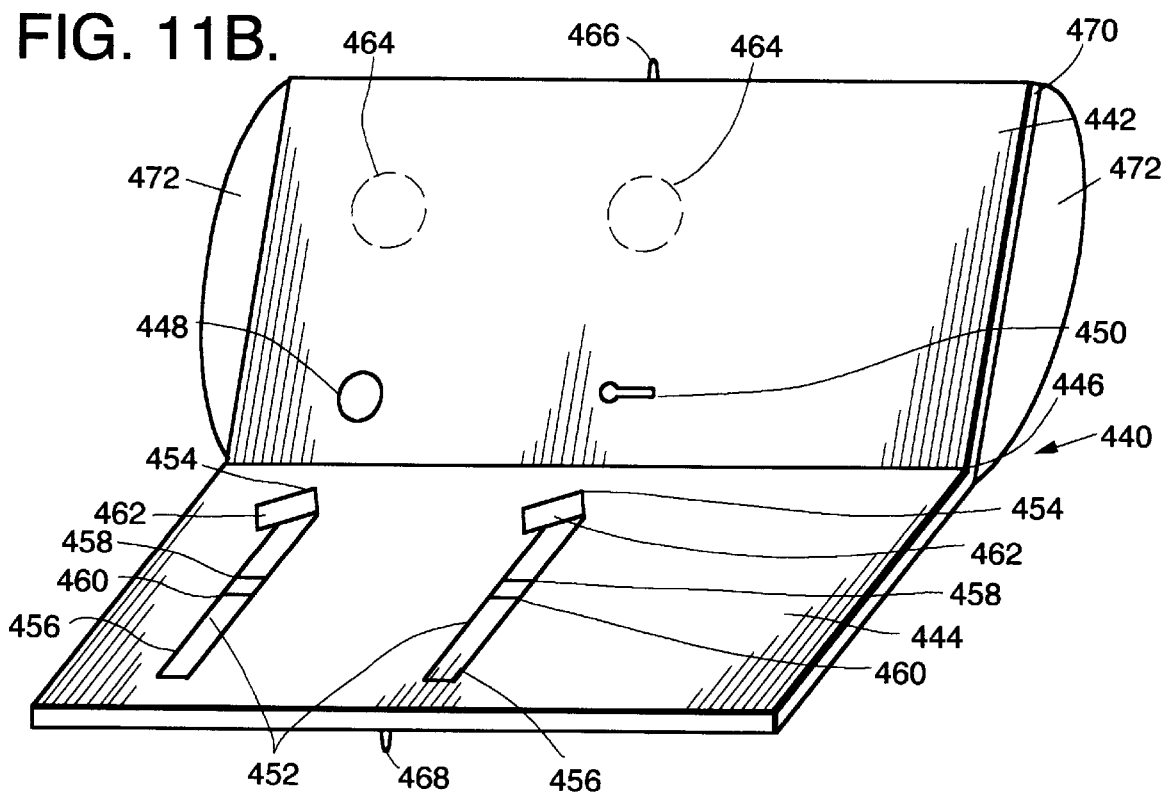

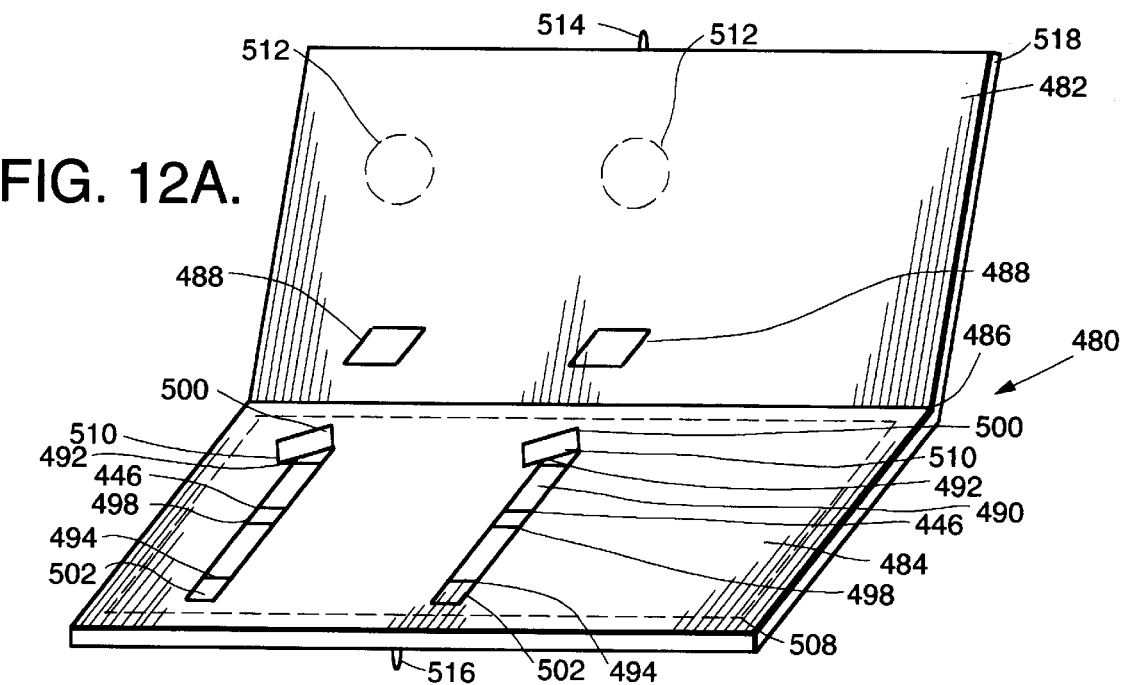
FIG. 12A.
FIG. 12B.
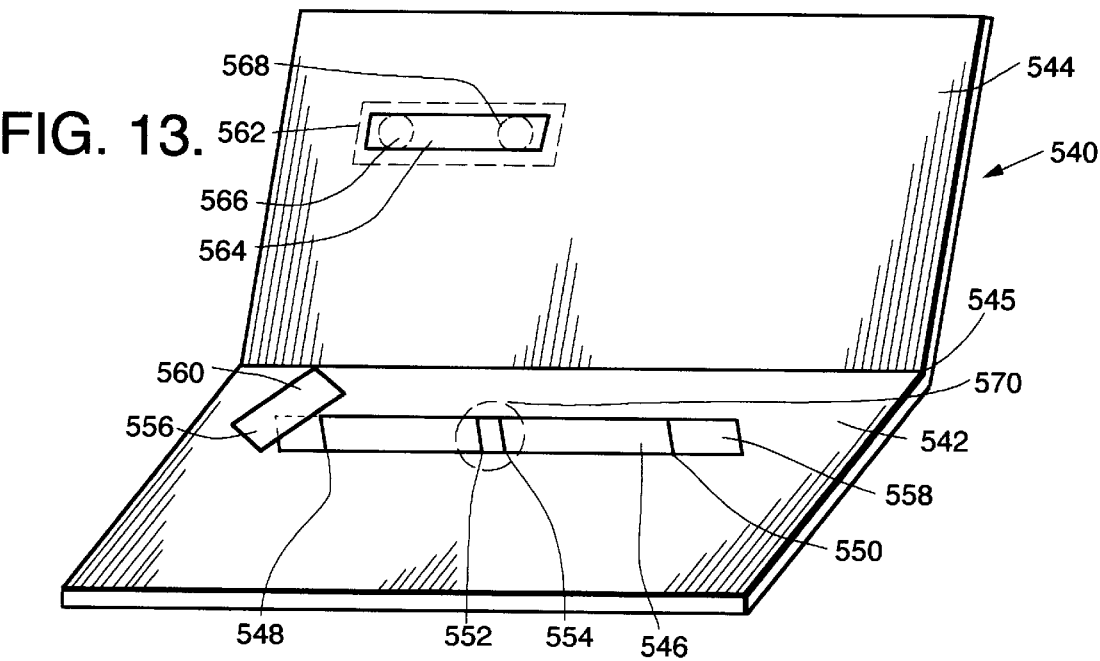
FIG. 13.

OPPOSABLE-ELEMENT ASSAY DEVICE EMPLOYING CONDUCTIVE BARRIER

CROSS-REFERENCES

This is a divisional of application Ser. No. 08/458,132 filed Jun. 6, 1995, which application(s) are incorporated herein by reference, which is a continuation-in-part of U.S. application Ser. No. 08/040,430, filed Mar. 31, 1993 (now abandoned), by Howard M. Chandler et al., entitled (as amended) "Opposable-Element Chromatographic Assay Device," which was a continuation-in-part of U.S. application Ser. No. 07/888,831, by Howard M. Chandler, filed May 27, 1992 (now abandoned), entitled "Assay Device," which was in turn a continuation-in-part of U.S. application Ser. No. 07/706,639 by Howard M. Chandler, filed May 29, 1991 (now abandoned), entitled (as amended) "Multiple Component Chromatographic Assay Device."

TABLE OF CONTENTS

For convenience, the following Table of Contents is provided:

BACKGROUND OF THE INVENTION
SUMMARY
BRIEF DESCRIPTION OF THE DRAWINGS
DESCRIPTION
Definitions
   I. CHROMATOGRAPHIC ASSAY DEVICES
      A. Principles of Devices and Methods According to the Present Invention
      B. Elements Common to Devices According to the Present Invention
         1. The Chromatographic Medium
         2. The Conductive Barrier
         3. Absorbers
         4. Other Fluid-Carrying Elements
         5. Opposable Components
         6. Labeled Components
      C. General Arrangement of Two-Component Devices
      D. Alternative Arrangements of Two-Component Devices
         1. Device with Sample Preparation Zone on First Opposable Component
         2. Device Including Two Separate Applicators on Same Opposable Component
         3. Device with Pad for Labeled Specific Binding Partner on Same Opposable Component as Chromatographic Medium
         4. Device with Detector Application Pad in Direct Contact with First End of Chromatographic Medium
         5. Device with Detector Application Pad on First Component
         6. Device with Two-Sector Applicator to Provide Wash
         7. Device with Two Detector Application Pads on Different Opposable Components
      D. Multiplex Assay Devices
         1. Basic Multiplex Device
         2. Multiplex Device with Collapsible Well
         3. Multiplex Device Adapted to Receive Test Card
   II. ANALYTES AND ANTIBODIES FOR USE WITH ASSAY DEVICES
   III. TEST KITS
      Example 1—Construction of Device for Detecting Streptococcal Antigen
      Example 2—Detection of Streptococcal Antigen Using Device of Example 1
      Example 3—Device for Detecting Hemoglobin in Fecal Occult Blood
ADVANTAGES OF THE INVENTION

BACKGROUND OF THE INVENTION

This invention is directed to test strips for determination of characteristics of samples, unitized housings, and kits incorporating the test strips, and methods of determining the characteristics of samples using the test strips.

Among the many analytical systems used for detection and/or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibodies to the bacterium *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers and anticonvulsants, and illegal drugs of abuse, such as cocaine, heroin, and marijuana; and (7) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium.

Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., *Am. J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or zone. This band or zone contains immobilized antibodies to the analyte of interest. The chromatographic medium often is in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al. both of which are incorporated herein by this reference.

In addition to immunochromatographic assays, it is also known to use enzyme-based chromatographic assays. These techniques are roughly analogous to immunochromatographic assays, but use an enzymatically catalyzed reaction instead of an antigen-antibody reaction. The enzymatically catalyzed reaction frequently generates a detectable product. Other analogous chromatographic assays are known.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to insure that the sample reaches the area where binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices such as pipettes. Each of these devices is then contaminated and must be disposed of using special precautions so that workers or people who may inadvertently come into contact with the waste do not become contaminated.

Accordingly, there is a need for an improved chromatographic device for the performance of immunochromatographic assays or other analogous assays. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the tests. This aspect of an improved assay device is particularly important in avoiding false negatives and false positives.

SUMMARY

I have developed an assay device that meets these needs and provides improved assays for analytes of biological interest, while simplifying the performance of the assay and avoiding contamination. The device can perform all types of immunoassays, including sandwich immunoassays, competitive immunoassays, and assays employing combinations of these principles. The device can perform serological assays in which the antigen to be detected is itself an antibody, such as antibody to *H. pylori*. The device can perform assays in which the antigen to be detected is detected indirectly by using a labeled second antibody binding to the first antibody to the analyte. These assay devices all include a conductive barrier attached to an opposable component of a device containing at least two opposable components.

An assay device according to the present invention makes use of pressure to transfer fluid from one opposable component to another opposable component, and also to drive fluid through the chromatographic medium. The pressure not only speeds up the operation of the device, but allows the performance of additional steps such as extraction steps to remove interfering particulate components within a single device. The pressure is generated by holding the opposable components together with engagers such as interlocking elements on each of the opposable components. Preferably, a predetermined pressure is applied to ensure the optimum performance of each step of the assay procedure.

Additionally, the device can perform other types of specific binding assays, such as: (1) assays based on the affinity of specific binding proteins such as lectins, hormone receptors, or viral receptors for their specific ligands; (2) assays based on the affinity of enzymes for their corresponding substrates or inhibitors; or (3) assays based on the affinity of a nucleic acid (DNA or RNA) segment for a complementary nucleic acid segment according to the Watson-Crick base pairing scheme.

In general, an assay device according to the present invention comprises:

(1) a first opposable component including a sample preparation means adapted to receive a liquid sample to be assayed;

(2) a second opposable component including a chromatographic medium having at least one reagent binding specifically to an analyte to be detected, the reagent being bound at a detection zone on the chromatographic medium, the second opposable component being attachable to the first opposable component; and (3) a conductive barrier attached to the second opposable component.

The first and second opposable components can be brought into opposition from a position in which they are not in opposition so as to cause the sample preparation means to apply the liquid sample to be tested to the chromatographic medium through the conductive barrier and to flow through the chromatographic medium. The chromatographic assay is performed as a result of migration of the sample within the chromatographic medium so that an analyte is detected within the chromatographic medium as the result of the migration by binding of a labeled reagent that binds specifically to the analyte to be detected. The analyte is detected at a position different than the position at which the sample is applied to the chromatographic medium. The analyte is detected on the chromatographic medium after migration by binding of the labeled reagent to the analyte bound to the detection zone.

Typically, the sample preparation means includes at least one reagent for the treatment of the sample before the sample is applied to the chromatographic medium. The reagent for treatment of the sample can be an extraction reagent to extract analyte from the sample.

Typically, the first and second opposable components each further comprise engaging means which secure the first and second opposable components in opposition. Typically, the first and second opposable components are joined by a hinge. Typically, the first and second opposable components are each substantially planar.

Generally, the detection zone is substantially smaller than the chromatographic medium. In this arrangement, the detection zone can contain a first specific binding partner to the analyte immobilized thereto. When the analyte is an antigen or a hapten, the first specific binding partner can be an antibody to the antigen or hapten. In one particularly preferred alternative, the analyte is human hemoglobin and the first specific binding partner is an anti-human hemoglobin antibody.

Alternatively, the analyte can be an antibody and the first specific binding partner can be a hapten or antigen capable of being bound specifically by the antibody.

Typically, the chromatographic medium further includes a control zone substantially smaller than the chromatographic medium. Typically, the control zone contains analyte immobilized thereto.

The chromatographic assay device can further comprise an absorbing means in operable contact with the second end of the chromatographic medium.

Typically, the sample preparation means further contains a specific binding partner for the analyte labeled with a detectable label in a form that can be resolubilized by the addition of a liquid to the sample preparation means. Generally, the liquid comprises an extraction reagent to extract analyte from the sample; however, other liquids can also be used.

In the assay device, at least one of the first and second opposable components can include an aperture therein for viewing of at least a portion of the chromatographic medium.

Typically, in assay devices according to the present invention, the first and second opposable components can be brought into opposition by direct manual closure from a position in which they are not in opposition. In assay devices according to the present invention, detection of the analyte typically occurs without contact of the sample with any additional liquid once the sample is applied to the chromatographic medium.

Another aspect of the present invention is a test kit for the detection and/or determination of an analyte. The test kit can comprise, separately packaged:

(1) the chromatographic assay device described above; and (2) a specific binding partner for the analyte labeled with a detectable label, the specific binding partner to be used with the chromatographic assay device.

Other devices according to the present invention can also be incorporated into test kits, comprising, separately packaged, the device, along with either a specific binding partner for the analyte labeled with a detectable label or a liquid for resolubilizing a resolubilizable labeled specific binding partner included in the device. In some cases, test kits can include a test card or an extraction reagent for extracting an analyte from a sample.

Preferably, the detectable label is a visually detectable label.

Another aspect of the present invention is a method for detecting and/or determining an analyte in a sample comprising the steps of:

(1) applying the sample to the sample preparation means of the chromatographic assay device described above;

(2) applying a detection reagent to the sample preparation means, the detection reagent including at least one component capable of binding specifically to analyte present in the sample;

(3) bringing the first and second opposable components into opposition so that the sample preparation means applies the sample and the detection reagent to the chromatographic medium through the conductive barrier;

(4) allowing the sample and the detection reagent to move through at least a portion of the chromatographic medium so that the detection reagent gives a detectable indication of the presence and/or quantity of the analyte; and (5) observing and/or measuring the detection reagent in at least a portion of the chromatographic medium in order to detect and/or determine the analyte.

In this method, preferably the detection reagent comprises a specific binding partner for the analyte labeled with a detectable label. Most preferably, the detectable label is a visually detectable label and the step of observing and/or measuring the detection reagent comprises visually observing the detection reagent.

Alternatively, if the sample preparation means further contains a specific binding partner for the analyte labeled with a detectable label in a form that can be resolubilized by the addition of a liquid to the sample preparation means, a method for detection of an analyte can comprise:

(1) applying the sample as a liquid to the sample preparation means of the chromatographic assay device, thereby resolubilizing the specific binding partner for the analyte with the detectable label so that the labeled specific binding partner can bind specifically to analyte present in the sample;

(2) bringing the first and second opposable components into opposition so that the sample preparation means applies the sample and the labeled specific binding partner to the chromatographic medium through the conductive barrier;

(3) allowing the sample and the labeled specific binding partner to move through at least a portion of the chromatographic medium so that the labeled specific binding partner gives a detectable indication of the presence and/or quantity of the analyte; and (4) observing and/or measuring the labeled specific binding partner in at least a portion of the chromatographic medium in order to detect and/or determine the analyte.

Methods of use of other assay devices according to the present invention, as described below, are analogous. The exact steps depend on the configuration of the assay device.

Yet another aspect of the present invention is a multiplex device capable of performing multiple assays on the same device simultaneously. In general, this device comprises:

(1) a first opposable component including a plurality of laterally separated sample preparation means, each adapted to receive a sample to be assayed;

(2) a second opposable component attachable to the first opposable component and including a chromatographic medium for each sample preparation means on the first opposable component, the chromatographic media being laterally separated; and (3) a plurality of conductive barriers each attached to the second opposable component, one for each chromatographic medium.

In this device, the first and second opposable components can be brought into opposition so as to cause each sample preparation means to apply each sample to be tested to the corresponding chromatographic medium through the corresponding conductive barrier.

In this multiplex device, at least one sample preparation means includes a collapsible well adapted for receiving a sample-containing device. If a collapsible well is included, the first opposable component can further include hingedly foldable wings that fold over the second opposable component when the first opposable component and second opposable component are brought into opposition.

An alternative embodiment of a multiplex assay device according to the present invention is adapted to receive a test card. This embodiment comprises:

(1) a first opposable component including a plurality of laterally separated reagent pads;

(2) a second opposable component adapted to receive a test card containing a plurality of dried specimens, the second opposable component including:

(a) a chromatographic medium for each sample preparation means on the first opposable component, the chromatographic media being laterally separated, each chromatographic medium having a first and a second end;

(b) a conducting means in operable contact with the first end of each chromatographic medium and in operable contact with each dried specimen of the test card when the test card is inserted into the second opposable component; and (c) an absorbing means in operable contact with the second end of each chromatographic medium; and (3) a plurality of conductive barriers each attached to the second opposable component, one for each chromatographic medium.

In this embodiment of a multiplex assay device according to the present invention, the first and second opposable components can be brought into opposition so as to cause each reagent pad to be applied to the corresponding dried specimen through the corresponding conductive barrier.

In this embodiment, each reagent pad can include a specific binding partner for the analyte labeled with a detectable label in a form that can be resolubilized by the addition of an aqueous reagent to the reagent pad. In one particularly preferred version of this embodiment, the analyte is human hemoglobin and the specific binding partner is an anti-human hemoglobin antibody.

Another embodiment of the present invention is an assay device in which the sample preparation means is located on the same opposable component as the chromatographic medium. This device comprises:

(1) a first opposable component including:

(a) a sample preparation means; and (b) a chromatographic medium in operable contact with the sample preparation means;

(2) a second opposable component attachable to the first opposable component including an application means containing a specific binding partner for the analyte labeled with a detectable label in a form that can be resolubilized by the addition of a liquid to the application means; and (3) a conductive barrier attached to the first opposable component.

In this device, bringing the first and second opposable components into opposition brings the application means into contact with the conductive barrier such that the labeled specific binding partner for the analyte is resolubilized by liquid passing through the conductive barrier. The chromatographic medium can have first and second ends with the conducting means being in operable contact with the first end of the chromatographic medium; in this arrangement, the first opposable component can further include an absorbing means in operable contact with the second end of the chromatographic medium.

Another embodiment of the present invention has two application means on the opposable component not including the chromatographic medium. This embodiment comprises:

(1) a first opposable component including:

(a) a chromatographic medium having first and second ends;

(b) a conducting means in operable contact with the first end of the chromatographic medium; and (c) an absorbing means in operable contact with the second end of the chromatographic medium;

(2) a second opposable component comprising:

(a) a first application means; and (b) a second application means; and (3) a conductive barrier attached to the first opposable component.

The first and second application means are positioned on the second opposable component such that they are not in operable contact when the first and second opposable components are not in opposition. Bringing the first and second opposable components into opposition places the conducting means in operable indirect contact with the first application means through the conductive barrier and places the conducting means in operable contact with the second application means, thereby placing the first and second application means in operable contact with each other.

Typically, in this embodiment, the first application means includes a sample application pad and the second application means comprises a detector application pad, to which detecting reagent can be applied, whereby, when the first and second opposable components are brought into opposition, the contents of the sample application pad and the detector application pad are applied to the conducting means through the conductive barrier. Generally, the detector application pad contains a first specific binding partner to the analyte in a form that can be resolubilized by addition of a liquid to the detector application pad, the first specific binding partner being labeled with a detectable label, and the chromatographic medium further comprises a detection zone substantially smaller in area than the chromatographic medium, the detection zone containing a second specific binding partner to the analyte immobilized thereto, such that a ternary complex comprising the first specific binding partner, the analyte, and the second specific binding partner (i.e., a sandwich complex) forms at the detection zone if analyte is present in the sample.

Another embodiment of an assay device according to the present invention has a detector application pad on the opposable component also having the chromatographic medium and a sample application pad on the other opposable component. This embodiment comprises:

(1) a first opposable component including:
  (a) a chromatographic medium having first and second ends;
  (b) a conducting means in operable contact with the first end of the chromatographic medium;
  (c) an absorbing means in operable contact with the second end of the chromatographic medium; and
  (d) a detector application pad in direct contact with the conducting means and positioned such that it is in indirect contact with the first end of the chromatographic medium;
(2) a second opposable component including a sample application pad; and
(3) a conductive barrier attached to the first opposable component.

In this embodiment, bringing the first and second opposable components into opposition causes the sample application pad to apply the sample to be tested to the detector application pad through the conductive barrier and thus to the first end of the chromatographic medium though the conducting means.

Yet another embodiment of the present invention comprises:

(1) a first opposable component including:
  (a) a chromatographic medium having first and second ends;
  (b) an absorbing means in operable contact with the second end of the chromatographic medium; and
  (c) a detector application pad in direct contact with the first end of the chromatographic medium; and
(2) a second opposable component including a sample application pad; and
(3) a conductive barrier attached to the first opposable component.

In this embodiment, when the first and second opposable components are brought into opposition, the detector application pad and the sample application pad are in indirect contact through the conductive barrier except for the region of the detector application pad directly adjacent to the first end of the chromatographic medium. Bringing the first and second opposable components into opposition causes the sample application pad to apply the sample to be tested to the detector application pad and thus to the first end of the chromatographic medium.

Yet another embodiment of an assay device according to the present invention comprises:

(1) a first opposable component including:
  (a) a chromatographic medium having first and second ends;
  (b) a detector application pad in operable contact with the first end of the chromatographic medium, the detector application pad containing at least one reagent for detection of the analyte;
  (c) a conductor for allowing the passage of fluid in operable contact with the detector application pad and in indirect contact with the first end of the chromatographic medium; and
  (d) an absorber for absorbing fluid in operable contact with the second end of the chromatographic medium;
(2) a second opposable component including a sample preparation zone for receiving a sample to be tested, the second opposable component being attachable to the first opposable component so that the first and second opposable components are brought into opposition and fluid is transferred from the second opposable component to the first opposable component; and
(3) a conductive barrier attached to the first opposable component.

In this embodiment, the first and second opposable components are configured so that a sample can be applied to the sample preparation zone on the second opposable component when the first and second opposable components are not in opposition and so that bringing the first and second opposable components into opposition results in the sample preparation zone being in indirect contact with the conductor to apply the sample to be tested through the conductive barrier to the conductor for flow through the conductor and then to the first end of the chromatographic medium through the detector application pad to add the reagent for detection of the analyte to the sample. The flow from the conductor through the detector application pad to the first end of the chromatographic medium is aided by absorption of fluid by the absorber.

Preferably, the detector application pad contains a first specific binding partner to the analyte in a form that can be resolubilized by addition of a liquid to the detector application pad, the first specific binding partner being labeled with a detectable label, and the chromatographic medium further comprises a detection zone substantially smaller in area than the area of the chromatographic medium, the detection zone containing a specific binding partner to the analyte immobilized thereto.

Another embodiment of an assay device according to the present invention includes two labeled specific binding partners. This embodiment comprises:

(1) a first opposable component including:
  (a) a chromatographic medium having first and second ends;
  (b) a first detector application pad in operable contact with the first end of the chromatographic medium, the first detector application pad containing a first specific binding partner to the analyte in a form that can be resolubilized by the addition of a liquid to the first detector application pad, the first specific binding partner being labeled with a detectable label;
  (c) a conductor for allowing the passage of fluid in operable contact with the first detector application pad so that the first detector application pad bridges the conductor and the first end of the chromatographic medium to allow fluid flow from the conductor through the first detector application pad and to the first end of the chromatographic medium; and
  (d) an absorber for absorbing fluid in operable contact with the second end of the chromatographic medium;
(2) a second opposable component attachable to the first opposable component so that the first and second opposable components are brought into opposition and fluid is transferred from the second opposable component to the first opposable component, the second opposable component including:
  (a) a sample preparation zone for receiving a sample to be assayed; and
  (b) a second detector application pad in operable contact with the sample preparation zone, the second detector application pad containing a second specific binding partner for the analyte in a form that can be resolubilized by the addition of a sample to the sample preparation zone, the second specific binding partner being labeled with a detectable label, the second detector application pad being located adjacent to the sample preparation zone on the second opposable component such that application of the sample to the sample preparation zone resolubilizes the second specific binding partner so that the sample preparation zone contains a mixture of the sample and the second specific binding partner; and (3) a conductive barrier attached to the first opposable component.

The first and second opposable components are configured so that a sample can be applied to the sample preparation zone on the second opposable component when the first and second opposable components are not in opposition. Bringing the first and second opposable components into opposition results in the sample preparation zone on the second opposable component being in operable indirect contact with the conductor on the first opposable component through the conductive barrier to apply the sample to be tested and the second specific binding partner to the conductor for flow through the conductor and then to the first end of the chromatographic medium through the first detector application pad to add the first specific binding partner to the sample and the second specific binding partner. The flow from the conductor through the first detector application pad to the first end of the chromatographic medium is aided by absorption of fluid by the absorber.

Typically, the first and second specific binding partners for the analyte in the first and second detector application pads are identical and the detectable labels labeling the first and second specific binding partners are identical.

Still another embodiment of an assay device according to the present invention has an applicator divided into two sectors. This embodiment comprises:

(1) a first opposable component including:
  (a) a chromatographic medium having first and second ends;
  (b) a conductor for allowing the passage of fluid in operable contact with the first end of the chromatographic medium; and
  (c) an absorber for absorbing fluid in operable contact with the second end of the chromatographic medium;

(2) a second opposable component attachable to the first opposable component so that the first and second opposable components are brought into opposition and fluid is transferred from the second opposable component to the first opposable component, the second opposable component including an applicator for applying fluid to the conductor on the first opposable component when the first and second opposable components are brought into opposition, the applicator divided into two sectors:
  (a) a first sector containing a first specific binding partner for the analyte in a form that can be resolubilized by the addition of a liquid to the applicator when the first and second opposable components are not in opposition, the first specific binding partner being labeled with a detectable label; and
  (b) a second sector lacking a first specific binding partner for the analyte; and (3) a conductive barrier attached to the first opposable component.

In this embodiment, the first and second opposable components are configured so that bringing the first and second opposable components into opposition places the first sector, but not the second sector of the applicator on the second opposable component into indirect contact with the conductor on the first opposable component through the conductive barrier, the second sector of the applicator being in indirect contact with the conductor through the first sector. This applies the contents of the first sector of the applicator to the chromatographic medium, and, subsequent to the application of the contents of the first sector of the applicator to the chromatographic medium, applies the contents of the second sector of the applicator to the chromatographic medium. The absorber withdraws fluid from the chromatographic medium to aid fluid flow from the applicator through the conductor and the chromatographic medium.

BRIEF DESCRIPTION OF THE DRAWINGS

These and other features, aspects, and advantages of the present invention will become better understood with reference to the following description, appended claims, and accompanying drawings where:

FIG. 2 is a drawing of a version of a two-component chromatographic assay device with a conductive barrier according to the present invention in which the first opposable component includes a sample preparation zone;

FIG. 3 is a drawing of another version of a two-component assay device with a conductive barrier according to the present invention with two applicators on the same opposable component;

FIG. 5 is a drawing of a variation of the two-component assay device shown in FIGS. 4A and 4B with the absorber on the second opposable component;

FIG. 6A is a drawing of yet another version of a two-component assay device according to the present invention, generally similar to the version of FIGS. 4A and 4B, but with the detector application pad in direct contact with the chromatographic medium;

FIG. 6B is a sectional rear view of the two-component assay device of FIG. 6A, showing details of the components in opposition;

FIG. 7 is a drawing of yet another version of a two-component assay device employing a conductive barrier according to the present invention, in which a detector application pad is on the first opposable component and is located between the chromatographic medium and a conductor;

FIG. 8 is a drawing of yet another version of a two-component assay device employing a conductive barrier according to the present invention, employing a two-sector applicator to provide a wash;

FIG. 9 is a drawing of yet another version of a two-component assay device employing a conductive barrier according to the present invention, with two detector application pads, one on each opposable component;

FIG. 10 is a drawing of a multiplex assay device according to the present invention, suitable for the simultaneous assay of one or more samples;

FIG. 11A is a drawing of another version of a multiplex assay device according to the present invention, containing a collapsible well to accommodate a sample;

FIG. 11B is a drawing of a version of a multiplex assay device similar to that of FIG. 11A, except substituting hingedly foldable wings for the gasket;

FIG. 12 is a drawing of a different version of a multiplex assay device according to the present invention adapted to receive a test card; and FIG. 13 is a drawing of an assay device according to the present invention suitable for receiving a swab or similar sampling device and designed for detection of Streptococcus A antigen as constructed in Example 1.

DESCRIPTION

Definitions

Figure 1A:
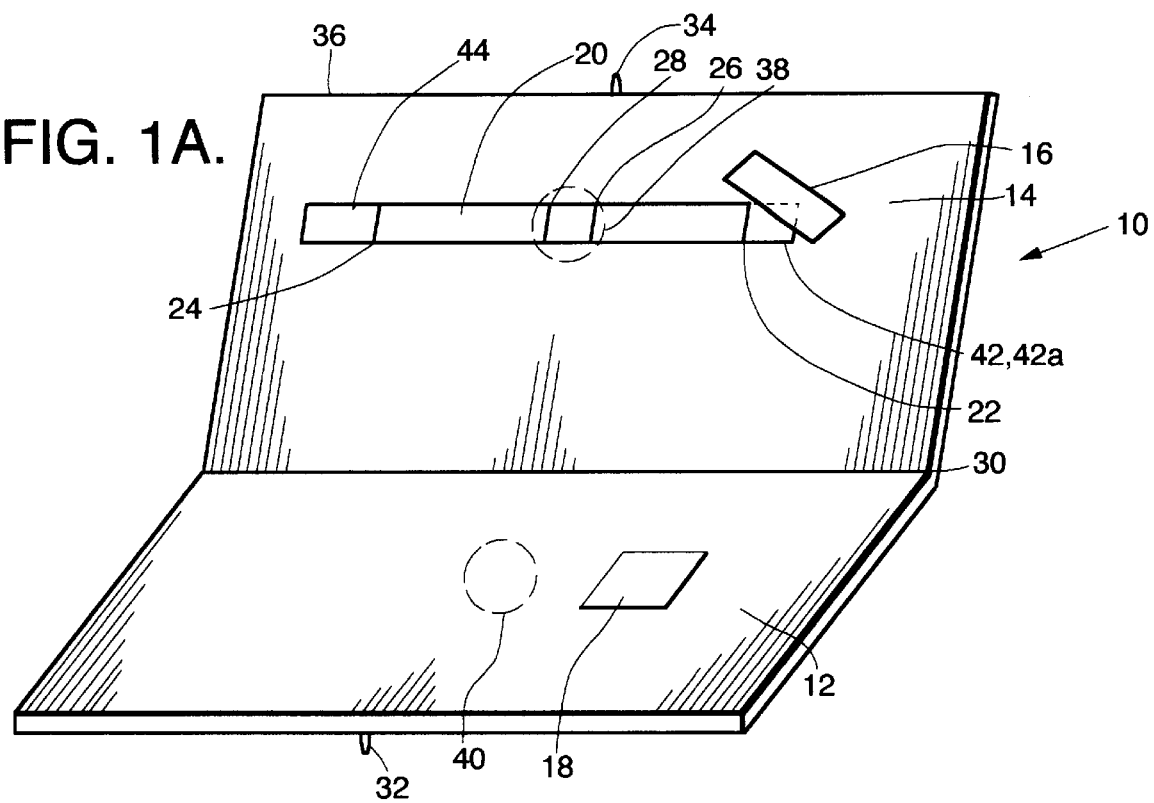
FIG. 1A is a drawing of one version of a two-component chromatographic assay device employing a conductive barrier according to the present invention.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that a liquid can flow from one of the two components to the other substantially uninterruptedly, by capillarity or otherwise. "Direct contact" means that the two elements are in physical contact, such as edge-to-edge or front-to-back. "Indirect contact" means that the two elements are not in physical contact, but are bridged by one or more conducting means. This bridging by one or more conducting means can be either edge-to-edge or front-to-back, such as by the opposition of planar elements.

Conductive Barrier: The term "conductive barrier" is used herein to describe an element that is capable of conducting liquids and solutes contained in the liquids while serving as a barrier to particulates and preventing liquid flow from one element to another except through the conductive barrier. As described below, such barriers can be constructed of cellulose, such as paper.

Finite Capacity: An absorbing means has finite capacity when it becomes saturated by liquid received during the normal performance of an assay in the device in which the absorbing means is located. At that point, the absorbing means can release additional liquid absorbed and become at least partially conductive.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits. Both polyclonal and monoclonal antibodies are included unless otherwise specified.

Secondary Specific Binding Partner: An additional specific binding partner that binds to a member of a pair of specific binding partners when the pair of specific binding partners is interacting is designated a secondary specific binding partner. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin.

I. CHROMATOGRAPHIC ASSAY DEVICES

One aspect of the present invention comprises chromatographic assay devices particularly useful for the assay of analytes in biological samples. These devices are suitable for the direct application of biological samples, without preliminary extraction steps, and are constructed so as to minimize interference with assay results caused by particulates or colored samples.

These devices include a conductive barrier attached to one of the opposable components that serves to provide a more even flow of material transferred from one opposable component to another opposable component. This provides a more reproducible assay and reduces the likelihood of false positive or false negative results.

The device has at least two substantially planar opposable components. One of the substantially planar components has on its surface a chromatographic medium.

When there are two opposable components, one of the opposable components is designated the first opposable component and the other is designated the second opposable component. This designation is arbitrary and for convenience in description; the role of each of the opposable components is determined by the element or elements located on it.

The device also has means for opposing the opposable components and applying pressure thereto. The opposable components can be brought into opposition from a position in which they are not in opposition by direct manual closure, i.e., by manipulation by the operator. The pressure applied is sufficient to transfer fluid from one opposable component to another opposable component in a direction substantially normal to the opposable components so that the sample is applied to the chromatographic medium for detection and/or determination of the analyte thereon. The pressure also drives fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components into opposition by engagers such as locks or clasps.

Devices according to the present invention can be constructed for the performance of either a sandwich or a competitive assay.

A type of assays for which devices according to the present invention are particularly useful is sandwich immunoassays. As used herein, the term "immunoassay" is used generally to include specific binding assays and need not necessarily be restricted to assays in which the specific binding partner is an antibody, unless so specified.

A. Principles of Devices and Methods According to the Present Invention

All of the devices according to the present invention have a chromatographic medium and have application of liquid to the chromatographic medium controlled by a conductive barrier. The barrier provides for smoother flow and prevents high local concentrations of analyte or, in some cases, a labeled specific binding partner, at a particular location on the chromatographic medium at the start of chromatography. This ensures even progress of chromatography and prevents retardation of the rate of chromatography as a result of analyte concentration.

Although the basic principle of the invention can be used in a single-component assay device, it is generally preferred to construct assay devices containing two or more opposable components connected by a hinge or other connection and fastenable by engagers such as locks. This allows pressure to be placed on the component to drive fluid from one component to another and to accelerate the rate of flow. The degree of pressure employed can be regulated so that it is optimum for the characteristics of the chromatographic medium, analyte, and label.

B. Elements Common to Devices According to the Present Invention

A number of elements are common to assay devices according to the present invention and are discussed here for convenience.

1. The Chromatographic Medium

The chromatographic medium is a strip. Typically, the strip is substantially planar, although this is not required in all applications. It is typically rectangular, having first and second ends and first and second surfaces. Throughout this description, the term "first end" refers to the end at or near which liquid is first applied to the chromatographic medium and the term "second end" applies to the opposite end of the chromatographic medium. The liquid applied at or near the first end of the chromatographic medium can be, but is not necessarily, a sample or a treated sample. The chromatographic medium is composed of material suitable as a medium for thin layer chromatography of analyte and analyte-antibody conjugates, such as nitrocellulose, nylon, rayon, cellulose, paper, or silica. The chromatographic medium can be pretreated or modified as needed. Typically, the chromatographic medium is translucent, so that colored zones appearing on it can be viewed from either side.

2. The Conductive Barrier

The conductive barrier is typically a thin layer of fibrous, porous material such as cellulose (i.e., paper) or nitrocellulose that is permeable to fluids and does not substantially absorb the fluids applied. Typically, the conductive barrier is rectangular or square. The conductive barrier is positioned in the assay device so that one side of the conductive barrier is in direct contact with one of the opposable components of the device and the other side is in direct contact with the second opposable component of the device. The conductive barrier has the characteristic that liquid applied to one side of the conductive barrier penetrates to the other side.

3. Absorbers

In a number of devices according to the present invention, absorbers are in operable contact with one or both ends of the chromatographic medium. The absorbers can be made of any bibulous material that will hold a liquid sufficiently so liquid can be drawn through the chromatographic medium and accumulated in the absorber. Typical materials include, but are not limited to, filter paper.

4. Other Fluid-Carrying Elements

As described below, in particular devices according to the present invention, other fluid-carrying elements can be employed as sample preparation zones, applicators, distribution membranes, and/or conductors. These elements are prepared of hydrophilic media that pass liquids without substantially absorbing them. Such materials are well-known in the art. In some cases, these elements can have incorporated therein a component in dry form that can be resolubilized by addition of a liquid to the element.

5. Opposable Components

Many of the embodiments of the assay device according to the present invention comprise two opposable components. The bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™.

The opposable components are joined by a hinge, preferably made of a material impermeable to liquids, such as a plastic that can be compatibly joined with or is the same as the material used for the first and second opposable components.

6. Labeled Components

For assay devices intended to perform a sandwich immunoassay, the labeled component is typically a labeled specific binding partner to the analyte. This labeled component is typically mobile, in that it can migrate through the chromatographic medium, whether free or bound to analyte. The label is preferably a visually detectable label, such as a colloidal metal label. Preferably, the colloidal metal label is gold, silver, bronze, iron, or tin; most preferably, it is gold. The preparation of gold-labeled antibodies and antigens is described in J. DeMey, "The Preparation and Use of Gold Probes," in *Immunocytochemistry: Modern Methods and Applications* (J. M. Polak and S. VanNoorden, eds., Wright, Bristol, England, 1986), ch. 8, pp. 115–145, incorporated herein by this reference. Antibodies labeled with colloidal gold are commercially available, such as from Sigma Chemical Company, St. Louis, Mo.

Alternatively, other colloidal labels, such as a colloidal sulfur label or a dye-silica label, can also be used. In a less preferred alternative, the visually detectable label can be a colored latex label. It is also possible to use other labels, such as a radioactive label or an enzyme label.

C. General Arrangement of Two-Component Device

In general, a two-component chromatographic assay device according to the present invention comprises:

(1) A first opposable component including a sample preparation zone adapted to receive a sample to be assayed; and (2) A second opposable component including a chromatographic medium; and (3) a conductive barrier attached to the second opposable component.

In this device, the first and second opposable components can be brought into opposition when the device is closed so as to cause a sample preparation zone to apply the sample to be assayed to the chromatographic medium. In use, the first and second opposable components are typically brought into opposition after a detection reagent is applied to the sample preparation zone. When the first and second opposable components are brought into opposition, the sample preparation zone applies the sample and detection reagent to the chromatographic medium through the conductive barrier so that the combination of sample and detection reagent is dispersed within the conductive barrier before being applied to the chromatographic medium. After the sample and detection reagent are allowed to traverse at least a portion of the chromatographic medium, the detection reagent gives a detectable indication of the presence and/or quantity of the analyte; the detection reagent is then observed and/or measured in at least a portion of the chromatographic medium to obtain this indication. This results in detection and/or determination of the analyte.

The description of the details of construction of this basic device also applies, as far as possible, to other two-component assay devices according to the present invention.

The detection reagent comprises the first specific binding partner for the analyte as described above; it may comprise additional components.

This process can give a qualitative and/or quantitative indication of the analyte, depending upon the concentration of the second specific binding partner in the detection zone and the size of the detection zone.

Typically, to achieve results, the assay requires from 30 seconds to 10 minutes, more typically, from 1 to 5 minutes, including any period of incubation of the sample on the sample preparation zone, as well as the time required for chromatography itself. Typically, the assay is performed at room temperature, although it can be performed at 4° C. or up to 37° C. or higher in some cases, depending upon the nature of the analyte and specific binding partners. In some cases, performing the assay at a lower temperature may be desirable to limit degradation, while in other cases, performing the assay at a higher temperature with suitable analytes and specific binding partners may speed up the assay.

In devices according to the present invention, detection of the analyte occurs without contact of the sample with any additional liquid once the sample is applied to the chromatographic medium. This is true even if a wash of sample is being used. In other words, the device is self-contained, and there is no need to dilute the sample or label with additional liquid once the sample is applied to the chromatographic medium. This provides optimum concentrations of sample and labeled specific binding partner for maximum sensitivity.

In devices according to the present invention, a chromatographic assay is performed as a result of migration of the sample within the chromatographic medium. The analyte is detected at a position different than the position at which the sample is applied to the chromatographic medium.

This general arrangement of the chromatographic assay device is shown in FIG. 1A. The chromatographic assay device 10 has a first opposable component 12, a second opposable component 14, and a conductive barrier 16 attached to the second opposable component 14. Typically, the conductive barrier 16 is flexibly attached to the second opposable component 14, such as by an adhesive that permits relative motion of the conductive barrier 16 and the second opposable component 14. In FIG. 1A and other figures, the conductive barrier 16 is shown, for convenience in depiction, separated from the second opposable component 14; however, during the operation of the device 10, the conductive barrier 16 is directly in contact with the second opposable component 14. The conductive barrier 16 can be attached to the second opposable component 14 by an edge of the conductive barrier 16.

The first opposable component 12 includes a sample preparation zone 18. The second opposable component 14 contains a chromatographic medium 20. The chromatographic medium 20 has a first end 22 and a second end 24; the chromatographic medium 20 contains a detection zone 26 and a control zone 28. The first opposable component 12 and the second opposable component 14 are joined by a hinge 30. The first and second opposable components 12 and 14 preferably further comprise engagers that secure the first and second opposable components in opposition. The engagers can comprise locks, such as locks 32 and 34 that are engaged when the first opposable component 12 and the second opposable component 14 are brought into opposition. The construction and dimensions of the locks 32 and 34 can be varied to exert the optimal degree of pressure on the opposable components 12 and 14. The degree of pressure that is optimal may depend on the thickness and construction of the chromatographic medium 20, the intended sample volume, and other factors. To guard against leakage of samples or reagents, a sealing ridge or gasket 36 is positioned around the perimeter of the first and second opposable components 12 and 14. Although the use of the engagers, such as the locks 32 and 34, and the use of the sealing ridge or gasket 36, is generally preferred, these components are not necessary to construct a basic device according to the present invention. The second opposable component 14 has a first window 38; optionally, the first opposable component 12 can have a second window 40 to permit viewing of the chromatographic medium 20 from either side. The second window 40 permits viewing of the chromatographic medium 20 from the surface opposite the surface to which the reagents are applied. As another option, the first window 38 can be absent and the second window 40 used for viewing of the chromatographic medium 20. Alternatively, the first and/or second opposable components 12 and 14 can be made of transparent or translucent materials, so that the chromatographic medium 20 can be viewed without a separate aperture or window.

Figure 1B:
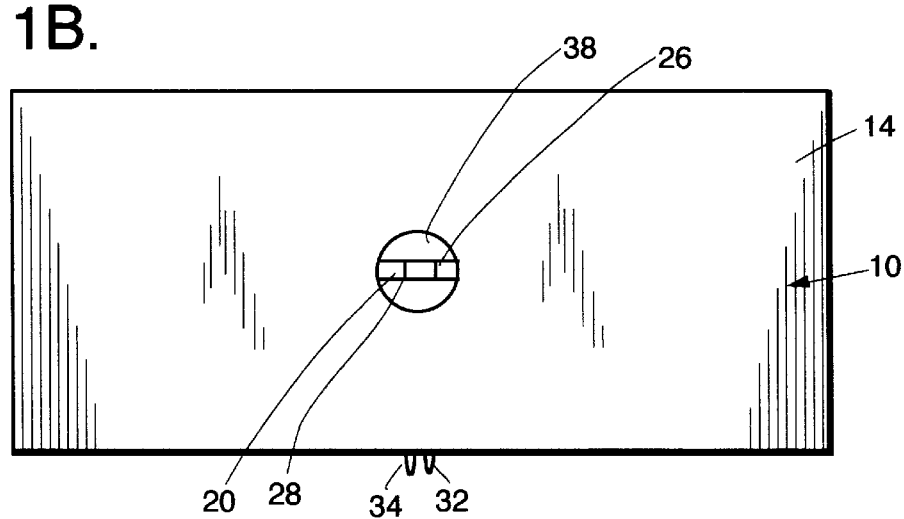
FIG. 1B is a drawing of the two-component chromatographic assay device of FIG. 1A shown with the two components having been brought into opposition.

FIG. 1B shows the device 10 after the opposable components 12 and 14 have been brought into opposition. The chromatographic medium 20, including the detection zone 26 and the control zone 28, is visible through window 38. The flow from the sample preparation zone 18 through the conductive barrier 16 contacts the chromatographic medium 20 at or near the first end 22 so that the contents of the sample preparation zone 18 can flow through the chromatographic medium 20, including the detection zone 26 and the control zone 28.

The device 10 can, optionally, further comprise a conductor 42 in operable contact with the first end 22 of the chromatographic medium 20, as shown in FIG. 1A. The conductor 42 can be a material such as cellulose or other material that can conduct a liquid without substantially absorbing it. The conductor 42 can be treated with a surfactant so that the reagents can be applied more evenly to the chromatographic medium 20. When the conductor 42 is present, the conductive barrier 16 preferably contacts the conductor 42 when the first and second opposable components 12 and 14 are brought into opposition.

Figure 1C:
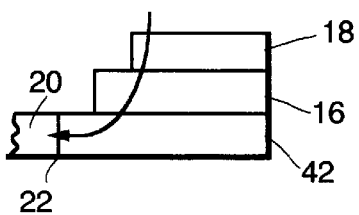
FIG. 1C is a side view of the device of FIGS. 1A and 1B showing the relationships of the sample preparation zone, the conductive barrier, and the conductor.

FIG. 1C shows, in greater detail, a side view of the device 10 with a conductor 42 after the first and second opposable components 12 and 14 have been brought into opposition, showing the approximate dimensional relationships of the sample preparation zone 18, the conductive barrier 16, and the conductor 42. Typically, the edge of the conductive barrier 16 extends past the edge of the sample preparation zone 18, and, in turn, the edge of the conductor 42 extends past the edge of the conductive barrier 16. This is to minimize or eliminate unwanted flow of reagents past these edges. The arrow in FIG. 1C indicates the flow path of fluid through the sample preparation zone 18, the conductive barrier 16, and the conductor 42.

The device 10 can further comprise an absorber 44 in operable contact with the second end 24 of the chromatographic medium 20 to aid in drawing fluid through the chromatographic medium 20 from the first end 22 toward the second end 24, as shown in FIG. 1A.

The sample preparation zone 18 can be made of any suitable material, such as, but not limited to, cellulose, paper, nylon, rayon, glass fiber, fleeces, or non-woven synthetic fabrics. The porosity of the sample preparation zone 18 can be chosen to filter out cellular or particulate matter in samples such as whole blood or fecal samples. The sample preparation zone 18 can contain at least one reagent for treatment of the sample before the sample is applied to the chromatographic medium 20 through the conductive barrier 16. The sample preparation zone 18 is adapted to receive a liquid sample. As used herein, the term "liquid sample" is defined to mean a sample having sufficient liquid so that chromatography can be performed, and includes semisolid samples or samples containing particulate matter.

The reagents that can be present in the sample preparation zone 18 vary with the sample to be applied to the sample preparation zone 18 and with the analyte to be assayed. They can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria to liberate analytes, substrates or coenzymes for enzymes, and the like. One particularly useful extraction reagent is a mixture of sodium nitrite and acetic acid to generate nitrous acid. The sodium nitrite can be present in dried form on the sample preparation zone 18, and the acetic acid can be added to the sample preparation zone 18 after the addition of the sample.

The sample, or optionally, a sampling device such as a throat swab or a microporous filter, can be placed by the operator on the sample preparation zone 18; if needed, other reagents can be added.

The bodies of the first and second opposable components 12 and 14 are preferably made of laminated cardboard that is sufficiently impervious to moisture to contain the liquids involved in the performance of the assay. Other cellulose-based materials, such as paperboard or solid bleached sulfite (SBS) can also be used. Alternatively, the bodies can be made of plastic that is impervious to moisture. A suitable plastic is a polycarbonate plastic such as Lexan™.

The hinge 30 is preferably made of material that is impermeable to a liquid, such as a plastic that can be compatibly joined with or is the same as the material used for the bodies of the first and second opposable components 12 and 14.

Typically, the chromatographic medium 20, absorber 44, conductor 42, conductive barrier 16, and other liquid-receiving components are secured to the bodies of the first and second opposable components 12 and 14 by adhesive. Suitable adhesives are well known in the art. Other joining methods, such as stapling or tacking, can also be used.

The analyte is detected either by means of a labeled specific binding partner to the analyte or by the use of a labeled secondary specific binding partner for a specific binding partner to the analyte that itself is unlabeled. In most cases, the use of a labeled specific binding partner to the analyte is preferred. The label of the labeled specific binding partner is preferably a visually detectable label, such as a colloidal metal label, as described above.

Alternatively, other colloidal labels, such as a colloidal sulfur label or a dye-silica label, can also be used. In a less preferred alternative, the visually detectable label can be a colored latex label. It is also possible to use other labels, such as radioactive labels.

Although Applicant does not necessarily intend to be bound by this theory, when a liquid containing a sample is applied to a resolubilizable specific binding partner labeled with a colloidal metal label, such as colloidal gold, the kinetics of the reaction between the analyte and the labeled specific binding partner are extremely rapid. These rapid kinetics result in the substantially complete labeling of analyte before the combination of the analyte and the labeled specific binding partner is applied to the chromatographic medium 20 through the conductive barrier 16. Thus, in a one-directional chromatographic procedure performed with an assay device according to the present invention, what is chromatographed is predominantly the binary complex of the analyte and the corresponding labeled specific binding partner. This allows separation of this complex from contaminants not binding the specific binding partner and improves accuracy of the assay.

In this embodiment, the labeled specific binding partner preferably is present on the sample preparation zone 18 in a form that can be resolubilized by the addition of a liquid to the sample preparation zone 18. Typically, the liquid is an aqueous liquid. Typically, the liquid is the sample itself. In some cases, particularly where small sample volumes are used, it may be desirable to add additional buffer or other liquid to the sample preparation zone.

In other embodiments discussed below, the labeled specific binding partner can be present on an element of the chromatographic assay device that is separate from the sample preparation zone but comes into contact with it during the performance of the assay. In these embodiments, the labeled specific binding partner is preferably present in a resolubilizable form on this element, and is resolubilized when the sample comes into contact with the element. In some cases, the labeled specific binding partner can be resolubilized by the addition of a separate liquid, distinct from the sample, to the element.

The chromatographic medium 20 on the second opposable component 14 is a flat strip. It is typically rectangular, having first and second ends 22 and 24. Throughout this Description, the term "first end" 22 refers to the end of the chromatographic medium 20 at which the sample is applied, and the term "second end" 24 refers to the opposite end. The direction of flow of the sample during the performance of the assay is from the first end 22 toward the second end 24 of the chromatographic medium 20. The chromatographic medium 20 is composed of a material suitable as a medium for thin-layer chromatography of analytes and analyte-antibody conjugates, such as nitrocellulose, nylon, rayon, cellulose, paper, or silica, as described above. The chromatographic medium 20 can be pretreated or modified as needed. Typically, the chromatographic medium 20 is translucent, so that colored zones appearing on it as a result of the assay can be viewed from either side.

In some applications, it is preferable to place a second flexible transparent support on the top of the chromatographic medium 20 to regulate the flow of the sample through the membrane and prevent migration over the top of the membrane. Suitable flexible transparent supports include polyethylene, vinyl, Mylar®, and cellophane.

When the chromatographic assay device 10 is to be used for an assay such as a sandwich immunoassay, the chromatographic medium 20 can further comprise a detection zone 26 substantially smaller than the chromatographic medium 20. This detection zone 26 can contain a second specific binding partner to the analyte immobilized thereto against diffusion. The second specific binding partner can be bound to the chromatographic medium by either covalent or non-covalent means; covalent means are generally preferred. If the analyte to be assayed is an antigen or hapten, the second specific binding partner can be an antibody to the antigen or the hapten. Alternatively, the analyte can be an antibody and the second specific binding partner can be a hapten or an antigen capable of being bound specifically by the antibody.

The chromatographic medium 20 can further comprise a control zone 28 substantially smaller than the chromatographic medium 20, and separate from the detection zone 20. The control zone 28 can comprise analyte immobilized thereto non-diffusibly in order to bind labeled antibody that is not bound at the detection zone 26 by the formation of a ternary "sandwich" complex. Any such antibody is bound by the immobilized analyte in the control zone 28 and forms a detectable zone or band at the control zone 28. This provides a check on the operation of the assay and the correct binding of the reagents, as described below. The methods used to bind the second specific binding partner in the detection zone 26 and the analyte in the control zone 28 are well known in the art and need not be described further.

Alternatively, for some analytes, such as carbohydrates, it may be difficult or impossible to fix the analyte stably to the chromatographic medium 20. In such cases, the control zone 28 can comprise an immobilized zone of antibody specific for the labeled anti-analyte antibody. For example, if the analyte is the Streptococcus A-specific carbohydrate, and the labeled antibody is rabbit IgG specific for Streptococcus A antigen, the control zone 28 can comprise goat antibody to rabbit IgG. In such cases, to prevent complete capture of the labeled anti-analyte antibody in the detection zone 26 at high analyte concentration and consequent disappearance of the labeled anti-analyte antibody from the control zone 28, it can be desirable to add labeled antibody not specific for the analyte and of a different species than the labeled anti-analyte antibody. Such antibody can constitute immunologically indifferent immunoglobulin or an antibody to an analyte not found in the test sample. The control zone 28 would then comprise anti-species antibody or analyte not found in the test sample.

Several variations of this device are possible. In one variation, as discussed above, the sample preparation zone 18 can further contain a specific binding partner for the analyte labeled with a detectable label in a form that can be resolubilized by the addition of a liquid to the sample preparation zone 18. The liquid can be the sample itself. The labeled specific binding partner can be freeze-dried or reversibly precipitated so that it is resolubilized and mobilized by the addition of the sample to the sample preparation zone. In this variation, it is not necessary to add a detection reagent to the sample preparation zone 18, as the detection reagent is automatically generated by the addition of the sample to the sample preparation zone 18.

In another variation, the conductor 42 in operable contact with the first end 22 of the chromatographic medium 20 on the second operable component 14 can be replaced by an absorber 42a of finite capacity in operable contact. The absorber 42a is located so that it comes into contact with the conductive barrier 16 when the first 12 and second 14 opposable components are placed into opposition, to apply the sample to the absorber 42a. This may be useful in controlling the flow of sample into the chromatographic medium 20 so that the chromatographic medium 20 is not overloaded.

In this version, the absorber 42a can contain a labeled specific binding partner for the analyte in a form that can be resolubilized, as described above. In this arrangement, the labeled specific binding partner is resolubilized when the first and second opposable components 12 and 14 are brought into opposition, applying the sample to the absorber 42a through the conductive barrier 16. The combination of the sample and the resolubilized labeled specific binding partner then enters the chromatographic medium 20 at its first end 22.

The use of the conductive barrier in assay devices according to the present invention provides a more regular and reproducible process of chromatography, by preventing excessively high local concentrations of reagents and assuring that the flow of reagents into and through the chromatographic medium is substantially synchronized.

D. Alternative Arrangements of Two-Component Device

The general principles of construction of the device shown in FIGS. 1A, 1B, and 1C, above, can also be used to construct other devices according to the present invention. Details of these devices are given below.

1. Device with Sample Preparation Zone on First Opposable Component

Another embodiment of a chromatographic assay device according to the present invention is a device that incorporates a sample preparation zone on the first opposable component, i.e., the component on which the chromatographic medium is located. Typically, in this embodiment, the second opposable component comprises an applicator incorporating a labeled specific binding partner for the analyte in a form that can be resolubilized. In this embodiment, a conductive barrier is attached to the first opposable component so that operable contact between the applicator and the sample preparation zone occurs through the conductive barrier.

In this embodiment, bringing the first and second opposable components into opposition brings the applicator into contact with the sample preparation zone through the conductive barrier so that the labeled specific binding partner for the analyte is resolubilized.

Preferably, the first opposable component further comprises a conductor, and operable contact between the sample preparation zone and the chromatographic medium is achieved by having the sample preparation zone and the chromatographic medium both in operable contact with the conductor.

Preferably, the first opposable component further comprises an absorber in operable contact with the second end of the chromatography medium.

The chromatographic medium is preferably constructed as described above, with detection and control zones.

This embodiment of the assay device is shown in FIG. 2. The chromatographic assay device 60 has a first opposable component 62 and a second opposable component 64. The first opposable component 62 includes a sample preparation zone 66, a conductor 68 in operable contact with the sample preparation zone 66, a chromatographic medium 70 having a first end 72 and a second end 74, and an absorber 76 in operable contact with the second end 74 of the chromatographic medium 70. The chromatographic medium 70 contains a detection zone 78 and a control zone 80. A conductive barrier 82 is attached to the first opposable component 62. The second opposable component 64 contains an applicator 84, preferably incorporating a labeled specific binding partner in a form that can be resolubilized. The first opposable component 62 and the second opposable component 64 are joined by a hinge 86. The second opposable component 62 contains a window 88 to allow viewing of at least a portion of the chromatographic medium 70. The first and second opposable components 62 and 64 have engagers such as locks 90 and 92, with a gasket 94 surrounding the first and second opposable components 62 and 64.

In operation, a sample is applied to the sample preparation zone 66. The first and second opposable components 62 and 64 are then brought into opposition so that the sample in the sample preparation zone 66 resolubilizes the contents of the applicator 84, including the labeled specific binding partner, the sample flowing through the conductive barrier 82. The contents of the sample preparation zone 66 and the applicator 84 are then applied to the chromatographic medium 70 through the sample preparation zone 66 and the conductor 68.

2. Device Including Two Separate Applicators on Same Opposable Component

Yet another embodiment of a chromatographic assay device according to the present invention including two separate applicators on the same opposable component. These two applicators are not in operable contact until they are bridged by a conductor on the opposing element when the elements are brought into opposition, operable contact again being made through the conductive barrier.

This embodiment of the chromatographic assay device is shown in FIG. 3. The chromatographic assay device 100 has a first opposable component 102 and a second opposable component 104. The first opposable component 102 includes a chromatographic medium 106 having a first end 108 and a second end 110, a conductor 112 in operable contact with the first end 108, and an absorber 114 in operable contact with the second end 110 of the chromatographic medium 106. The chromatographic medium 106 contains a detection zone 116 and a control zone 118. A conductive barrier 120 is attached to the first opposable component 102. The second opposable component 104 contains a first applicator (sample application pad) 122 and a second applicator (detector application pad) 124. The first applicator 122 and the second applicator 124 are not in operable contact until the first opposable component 102 and the second opposable component 104 are brought into opposition. When the first opposable component 102 and the second opposable component 104 are brought into opposition, the first applicator 122 is brought into operable contact with the conductor 112 through the conductive barrier 120 and the second applicator 124 is brought into operable contact with both the conductor 112 and the first end 108 of the chromatographic medium 106 through the conductive barrier 120. The overlap is typically several millimeters; i.e., enough to ensure transfer of fluid. This results in the first applicator 122 and the second applicator 124 being bridged by the conductor 112 so that the contents of the first applicator 122 and the second applicator 124 are applied to the chromatographic medium 106. The first opposable component 102 and the second opposable component 104 are joined by a hinge 126. The second opposable component 104 contains a window 128 to allow viewing of the chromatographic medium 106. The first and second opposable components 102 and 104 also include engagers such as locks 130 and 132 and a gasket 134.

The first applicator 122 can comprise a sample application pad and the second applicator 124 can comprise a detector application pad, to which detecting reagent can be applied. The term "detector application pad", as used herein, refers to a component that contains a detection reagent, typically a labeled specific binding partner for the analyte. The use of the term "detector application pad" is not intended to imply that detection occurs in this component; typically, detection occurs in the detection zone of the chromatographic medium.

When the first and second opposable components 102 and 104 are brought into opposition, the contents of the sample application pad and the detector application pad are applied to the chromatographic medium 106 via the conductive barrier 120 and then via the conductor 112.

Preferably, the second applicator 124 (detector application pad) contains a specific binding partner for the analyte labeled with a detectable label in a form that can be resolubilized by the addition of a liquid to the second applicator 124. The liquid is typically the sample itself, which resolubilizes the labeled specific binding partner when the first 102 and second 104 opposable components are brought into opposition. In some assays, it may be desirable to add a separate reconstituting liquid to the detector application pad. Alternatively, the labeled specific binding partner can be applied in liquid form to the second applicator 124.

3. Device with Pad for Labeled Specific Binding Partner on Same Opposable Component as Chromatographic Medium Yet another embodiment of a chromatographic assay device according to the present invention is a two-component device incorporating a pad for a labeled specific binding partner on the same opposable component as the chromatographic medium. In this device, the sample applicator is located on the other opposable component.

Figure 4A:
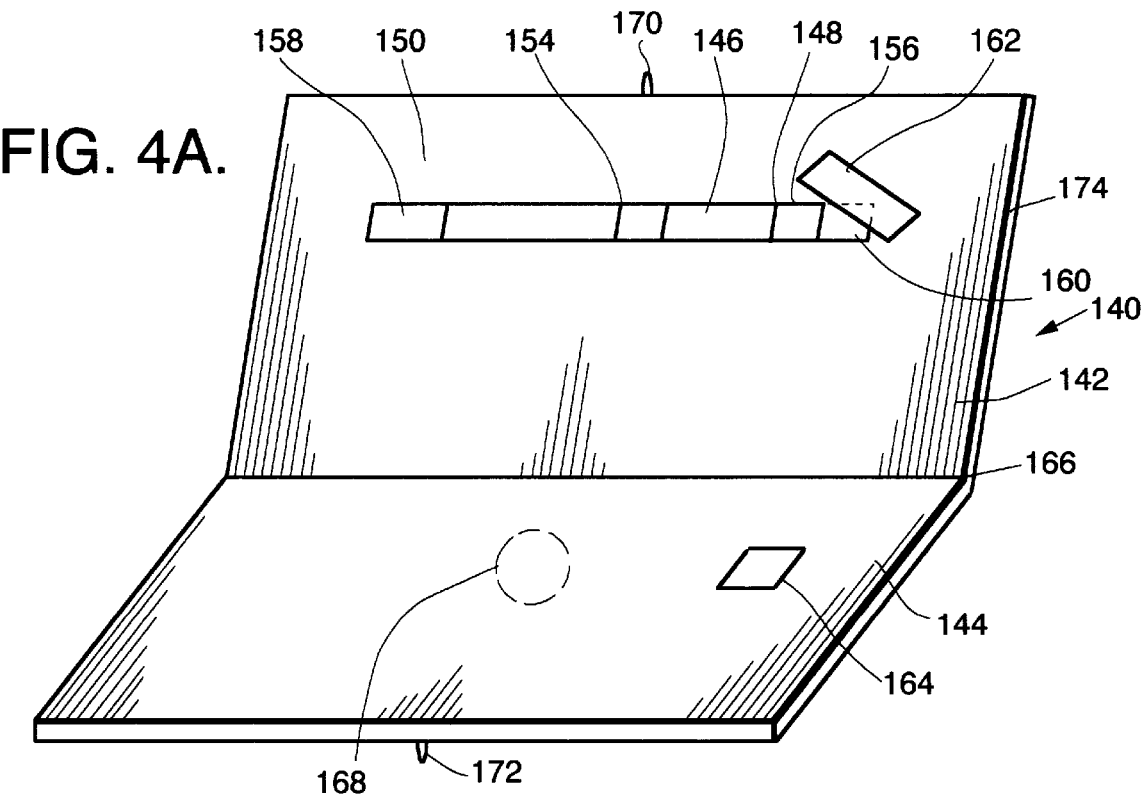
FIG. 4A is a drawing of another version of a two-component assay device with a conductive barrier according to the present invention incorporating a pad for a labeled specific binding partner on the same opposable component as the chromatographic medium and a sample preparation zone on the other opposable component.

This embodiment of a chromatographic assay device according to the present invention is depicted in FIG. 4A. The chromatographic assay device 140 has a first opposable component 142 and a second opposable component 144. The first opposable component 142 has a chromatographic medium 146 having a first end 148 and a second end 150. The chromatographic medium 146 has a detection zone 152 and, optionally, a control zone 154, as described above for other variations of assay devices suitable for sandwich immunoassays. The first opposable component 142 also has a conductor 156 in operable contact with the first end 148 of the chromatographic medium 146, and an absorber 158 in operable contact with the second end 150 of the chromatographic medium 146. The first opposable component 142 also has a detector application pad 160 in direct contact with the conductor 156 and positioned such that it is in indirect contact with the first end 148 of the chromatographic medium 146. Attached to the first opposable component 142 is a conductive barrier 162. The second opposable component 144 has a sample application pad 164. The first opposable component 142 and the second opposable component 144 are joined by a hinge 166. When the first opposable component 142 and the second opposable component 144 are brought into opposition, the sample application pad 164 is brought into operable contact with the detector application pad 160 through the conductive barrier 162. The second opposable component 144 contains a window 168 to allow viewing of the chromatographic medium 146. The first and second opposable components 142 and 144 have engagers such as locks 170 and 172, and a gasket 174, as described above.

Figure 4B:
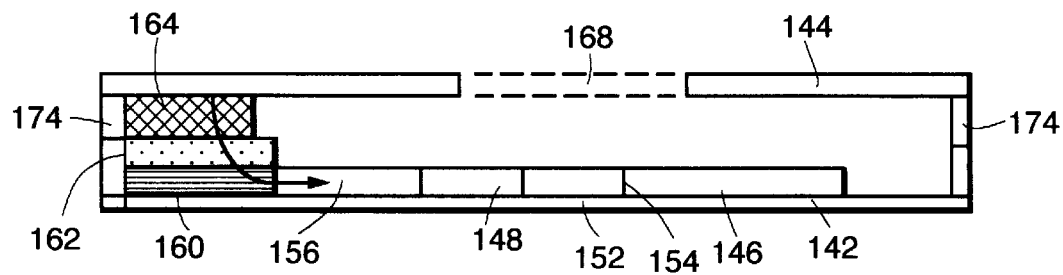
FIG. 4B is a sectional rear view of the two-component assay device of FIG. 4A, showing details of the chromatographic medium, the first and second opposable components, and the conductive barrier.

A sectional rear view of the device 140 is depicted in FIG. 4B. The section shown in FIG. 4B is taken from the view of FIG. 4A, between the chromatographic medium 146 and the hinge 166 looking toward the edge opposite the hinge 166. FIG. 4B shows the first opposable component 142 and second opposable component 144 in opposition, with the conductive barrier 162 between them. The sample application pad 164 is shown in indirect contact with the detector application pad 160 through the conductive barrier 162. The detector application pad 160 is in contact with the conductor 156, which is in turn in contact with the first end 148 of the chromatographic medium 146. The detection zone 152 and control zone 154 of the chromatographic medium 146 are shown. The second end 150 of the chromatographic medium 146, nearer the control zone 154, is in contact with the absorber 158. The arrow in FIG. 4B indicates the flow path of fluid through the sample application pad 164, the conductive barrier 162, and the detector application pad 160.

Bringing the first and second opposable components 142 and 144 into opposition causes the sample application pad 164 to apply the sample to be tested to the detector application pad 160 through the conductive barrier 162 and thus to the first end 148 of the chromatographic medium 146 though the conductor 156.

Preferably, the detector application pad 160 contains a first specific binding partner to the analyte in a form that can be resolubilized by addition of a liquid to the detector application pad 160, and the first specific binding partner is labeled with a detectable label.

Preferably, the contents of the sample application pad 164 after a sample is applied thereto comprises a liquid, and the liquid applied to the detector application pad 160 comprises the contents of the sample application pad. In this arrangement, there is no additional liquid needed to resolubilize the labeled specific binding partner.

In a variation of this device, the absorber is located on the second opposable component instead of being located on the first opposable component. The absorber is separated from the sample application pad also located on the second opposable component and is placed in operable contact with the second end of the chromatographic medium when the first opposable component and the second opposable component are brought into opposition. This variation of the device is shown in FIG. 5. In FIG. 5, all elements of the device are the same as in FIG. 4 except that the absorber 158 is relocated to the second opposable component 144 and comes into operable contact with the second end 150 of the chromatographic medium 146 when the first and second opposable components 142 and 144 are brought into opposition. This allows for the use of a larger absorber. The advantages of a larger absorber include the ability to use a larger sample volume, so that dilute samples can be assayed. This can provide a greater dynamic range for the assay.

4. Device with Detector Application Pad in Direct Contact with First End of Chromatographic Medium A further variation of this device omits the conductor between the detector application pad and the chromatographic medium, so that the detector application pad is in direct contact with the first end of the chromatographic medium. In this variation, when the first and second opposable components are brought into opposition, the detector application pad and the sample application pad are in operable contact through the conductive barrier except for the region of the detector application pad directly adjacent to the first end of the chromatographic medium. There is a slight gap or offset at that region of the detector application pad, so that sample cannot flow directly from the sample application pad or conductive barrier to the chromatographic medium. This gap or offset is typically from about 0.5 mm to about 2 mm, more typically from about 0.5 mm to about 1 mm.

This variation is particularly suitable for the detection of fecal occult blood by use of a labeled anti-hemoglobin antibody, without the occurrence of false negatives due to a high dose "hook" effect. It can also be used for other analytes.

This variation is depicted in FIG. 6A. The chromatographic assay device 200 has a first opposable component 202 and a second opposable component 204. The first opposable component 202 has a chromatographic medium 206 having a first end 208 and a second end 210. The chromatographic medium 206 has a detection zone 212 and a control zone 214. The first opposable component 202 also has an absorber 216 in operable contact with the second end 210 of the chromatographic medium 206. The first opposable component 202 also has a detector application pad 218 in direct contact with the first end 208 of the chromatographic medium 206. Attached to the first opposable component 202 is a conductive barrier 220.

The second opposable component 204 has a sample application pad 222. The first opposable component 202 and the second opposable component 204 are joined by a hinge 224. When the first opposable component 202 and the second opposable component 206 are brought into opposition, the sample application pad 222 is brought into contact with the detector application pad 218 through the conductive barrier 220, except for a narrow gap or offset 226 at the end of the detector application pad 218 in contact with the first end 208 of the chromatographic medium 206. This gap 226 prevents sample applied to the sample application pad 222 from flowing directly into the chromatographic medium 206. The second opposable component 204 has a window 228 to allow viewing of the chromatographic medium 206. The first and second opposable components 202 and 204 have engagers such as locks 230 and 232, and a gasket 234 as described above.

A sectional rear view of the device 200 of FIG. 6A is depicted in FIG. 6B. The section shown in FIG. 6B is taken from the view of FIG. 6A between the chromatographic medium 206 and the hinge 224 looking toward the edge opposite the hinge 224. FIG. 6B shows the first opposable component 202 and second opposable component 204 in opposition, with the conductive barrier 220 between them and with the hinge 224 in closed position. The sample application pad 222 is shown in indirect contact with the detector application pad 218, except for the small gap 226 at the end of the detector application pad 218 nearest the chromatographic medium 206. The detector application pad 218 is in direct contact with the first end 208 of the chromatographic medium 206. The detection zone 212 and control zone 214 of the chromatographic medium 206 are shown. The second end 210 of the chromatographic medium 206, nearer the control zone 214, is in contact with the absorber 216.

5. Device with Detector Application Pad on First Component

Another embodiment of a two-component chromatographic assay device according to the present invention has a detector application pad located on the first opposable component and a sample preparation zone located on the second opposable component. In this device, the detector application pad is located so that it is in operable contact with the first end of the chromatographic medium. The detector application pad preferably contains a labeled specific binding partner to the analyte in a form that can be resolubilized by the addition of a liquid to the detector application pad. The device further comprises a conductor in operable contact with the detector application pad and in indirect contact with the first end of the chromatographic medium, as well as an absorber in operable contact with the second end of the chromatographic medium.

In the operation of this embodiment of the device, the sample is applied to the sample preparation zone on the second opposable component, after which the first and second opposable components are brought into opposition. This applies the contents of the sample preparation zone to the conductor through the conductive barrier, and then to the first end of the chromatographic medium through the detector application pad. When the sample reaches the detector application pad, the contents of the detector application pad are resolubilized. When the contents of the detector application pad include a specific binding partner for the analyte, the passage of the sample through the detector application pad results in the specific binding partner binding to any analyte present in the sample.

This embodiment of the device is shown in FIG. 7. The assay device 240 has a first opposable component 242 and a second opposable component 244. The first opposable component 242 includes a chromatographic medium 246 having a first end 248 and a second end 250. The first opposable component 242 also includes a detector application pad 252 in operable contact with the first end 248 of the chromatographic medium 246, a conductor 254 in operable contact with the detector application pad 252 and in indirect contact with the first end 248 of the chromatographic medium 246, and an absorber 256 in operable contact with the second end 250 of the chromatographic medium 246. The chromatographic medium 246 includes a detection zone 258 and a control zone 260. Attached to the first opposable component 242 is a conductive barrier 262.

The second opposable component 244 includes a sample preparation zone 264. The first and second opposable components 242 and 244 are joined by a hinge 266. The second opposable component 244 has an aperture 268 to permit viewing of at least a portion of the chromatographic medium 246. The first and second opposable components 242 and 244 include engagers 270 and 272, and a gasket 274 as described above.

A variation of this embodiment incorporates a specific binding partner for the analyte in a form that can be resolubilized on the second opposable component 244 as well as on the first opposable component 242. When the resolubilizable specific binding partner is located on the second opposable component 244, it is preferably not located directly in the sample preparation zone 264 itself. Rather, it preferably surrounds the sample preparation zone 264 in an area 276 such that the sample first passes through the sample preparation zone 264 and then moves into the area 276 surrounding the sample preparation zone 264, resolubilizing the specific binding partner. For example, the sample preparation zone 264 can comprise a piece of suitably treated filter paper placed on the surface of the second opposable component 244, adhered by an adhesive or a fastener. This allows for treatment of the sample, e.g., to adjust the pH, lyse intact cells, and/or remove particulates, before the sample contacts the resolubilizable specific binding partner. This variation of this embodiment can provide a wider dynamic range and can be useful when the available antibody has a low affinity or low concentrations of analytes are to be detected.

6. Device with Two-Sector Applicator to Provide Wash

Another embodiment of a two-component assay device according to the present invention has a two-sector applicator to provide a wash of sample unreacted with the labeled specific binding partner after the mixture of the sample and the labeled specific binding partner has passed through the chromatographic medium. This embodiment has the advantage of providing a clearer background and making it easier to read a weakly positive result.

In this embodiment, the first opposable component includes a chromatographic medium having first and second ends, a conductor in operable contact with the first end of the chromatographic medium, and an absorber in operable contact with the second end of the chromatographic medium. The second opposable component includes an applicator divided into two sectors: a first sector containing a labeled specific binding partner for the analyte in resolubilizable form, and a second sector without the labeled specific binding partner. Bringing the first and second opposable components into opposition places the first sector, but not the second sector, of the applicator into indirect contact with the conductor through the conductive barrier, to apply the contents of the first sector of the applicator to the conductor and then to the first end of the chromatographic medium. The second sector is placed in indirect contact with the conductor, as the contents of the second sector flow through the first sector and then to the conductor via the conductive barrier. Thus, subsequent to the application of the contents of the first sector of the applicator to the conductor, the contents of the second sector are applied to the conductor. The contents of the second sector, which includes sample but no labeled specific binding partner, serve to wash out unbound labeled specific binding partner from the chromatographic medium, thereby reducing the background of visible label seen in the chromatographic medium and improving the reading of the assay device. This is particularly advantageous for weakly positive assays.

This embodiment of the assay device is shown in FIG. 8. The assay device 300 has a first opposable component 302 and a second opposable component 304. The first opposable component 302 includes a chromatographic medium 306 with a first end 308 and a second end 310, a conductor 312 in operable contact with the first end 308 of the chromatographic medium 306, and an absorber 314 in operable contact with the second end 310 of the chromatographic medium 306. Attached to the first opposable component 302 is a conductive barrier 316.

The second opposable component 304 has an applicator 318 divided into two sectors: a first sector 320 in direct contact with the conductor 312 when the first and second opposable components 302 and 304 are brought into opposition, and a second sector 322 in indirect contact with the conductor 312 when the first and second opposable components 302 and 304 are brought into opposition.

The chromatographic medium 306 has a detection zone 324 and a control zone 326. The first and second opposable components 302 and 304 are joined by a hinge 328. The second opposable component 304 has a window 330 to permit viewing of at least a portion of the chromatographic medium 306. The first and second opposable components 302 and 304 also include engagers 332 and 334 and a gasket 336, as described above.

7. Device with Two Detector Application Pads on Different Opposable Components

Yet another embodiment of a two-component assay device according to the present invention incorporates two separate detector application pads on different opposable components. This arrangement is particularly useful when it is desired to use a relatively large volume of a labeled specific binding partner, as when a labeled antibody is only available in dilute form and attempts to concentrate the antibody would denature or inactivate it.

This embodiment of the two-component chromatographic assay device is depicted in FIG. 9. The chromatographic assay device 350 has a first opposable component 352 and a second opposable component 354 connected by a hinge 356. The first opposable component 352 includes a chromatographic medium 358 having a first end 360 and a second end 362. The chromatographic medium 358 includes a detection zone 364, and, optionally, a control zone 366.

The first opposable component 352 also has a first detector application pad 368 in operable contact with the first end 360 of the chromatographic medium 358. The first detector application pad 368 contains a first specific binding partner to the analyte in a form that can be resolubilized by the addition of a liquid to the first detector application pad 368. The first specific binding partner is typically labeled with a detectable label. The first opposable component 352 also has a conductor 370 in operable contact with the first detector application pad 368 so that the first detector application pad 368 bridges the conductor 370 and the first end 360 of the chromatographic medium 358. The first opposable component 352 also has an absorber 372 in operable contact with the second end 362 of the chromatographic medium 358. Attached to the first opposable component 352 is a conductive barrier 374.

The second opposable component 354 includes a sample preparation zone 376 for receiving a sample to be assayed. The second opposable component 354 also contains a second detector application pad 378 in operable contact with the sample preparation zone 376, with the sample preparation zone 376 being placed over the second detector application pad 378. The sample preparation zone 376 and the second detector application pad 378 can be held together by a fastener or adhesive. The second detector application pad 378 and the sample preparation zone 376 are positioned so that a sample applied to the sample preparation zone 376 must pass through the sample preparation zone 376 before entering the second detector application pad 378. The second detector application pad 378 contains a second specific binding partner for the analyte in a form that can be resolubilized by the addition of a sample to the sample preparation zone 376. The second detector application pad 378 is positioned such that application of the sample to the sample preparation zone 376 resolubilizes the second specific binding partner so that the sample preparation zone 376 contains a mixture of the sample and the second specific binding partner.

The second specific binding partner is labeled with a detectable label. Preferably, the first and second specific binding partners are identical and the detectable labels labeling the first and the second specific binding partners are identical.

The second opposable component 352 also contains an aperture 380 therein to allow viewing of at least a portion of the chromatographic medium 358, including the detection zone 364 and, if present, the control zone 366. The first and second opposable components 352 and 354 also have engagers such as locks 382 and 384, and a gasket 386 as described above for the basic two-component device including a conductive barrier.

When the first and second opposable components 352 and 354 are brought into opposition, the sample preparation zone 376 is brought into contact with the conductive barrier 374 to apply the sample and the second specific binding partner to the conductor 370 and then to the first end 360 of the chromatographic medium 358 through the first detector application pad 368, via the conductive barrier 374. Thus, the sample sequentially contacts the second specific binding partner and then the first specific binding partner before being applied to the first end 360 of the chromatographic medium 358 for chromatography. This results in a greater volume of labeled specific binding partner being in contact with the sample to increase the sensitivity of the assay.

E. Multiplex Assay Devices

The description of the devices above is directed to assay devices that perform one assay at a time. However, assay devices according to the present invention can also be constructed that can perform multiple assays at the same time. The assays can be performed for the same analyte or different analytes. In general, all versions of the device described above are suitable for multiplex use by providing first and second opposable components with multiple chromatographic media, sample preparation zones, conductive barriers, applicators, conductors, absorbers, and other required elements. The following descriptions of multiplex devices according to the present invention are therefore intended to be exemplary and not exclusive.

1. Basic Multiplex Device

One version of a multiplex assay device according to the present invention is shown in FIG. 10. The assay device 400 has a first opposable component 402 and a second opposable component 404. The second opposable component 404 is hingedly attached to the first opposable component 402 by a hinge 406. The first opposable component 402 comprises a plurality of chromatographic media 408. Each of the chromatographic media 408 has a first end 410 and a second end 412, and includes a detection zone 414 and a control zone 416. The second end 412 of each chromatographic medium 408 is in operable contact with an absorber 418 to drive flow through the chromatographic medium 408. There is a separate absorber 418 for each chromatographic medium 408. Attached to the first opposable component 402 is a plurality of conductive barriers 420. The conductive barriers 420 can be physically separate; alternatively, they can be combined in one single structure and functionally isolated by substantially impermeable barriers.

The second opposable component 404 comprises a plurality of sample preparation zones 422, one for each chromatographic medium 408. Typically, each sample preparation zone 422 contains labeled specific binding partner for the analyte to be tested in a form that can be resolubilized by the addition of a liquid sample to the sample preparation zone 422. Alternatively, the labeled specific binding partner in a liquid form can be added to the sample preparation zone 422 before or after the addition of the sample thereto. Bringing the first and second opposable components 402 and 404 into opposition causes each of the sample preparation zones 422 to be applied to the corresponding chromatographic medium 408 at the first end 410. The second opposable component 404 contains a plurality of apertures 424, one for each chromatographic medium 408. The first opposable component 402 and second opposable component 404 include engagers 426 and 428 and a gasket 430, as described above.

This multiplex device can contain from 2 to 12 or more sample preparation zones and chromatographic media, depending upon the assay for which the device is to be employed. Typically, the device contains from 2 to 5 separate sample preparation zones and chromatographic media.

This embodiment of the device can be used to assay a number of different analytes in different aliquots of the same sample, or can be used to assay the same analyte in a number of different samples. This latter mode is particularly useful in assaying for a condition for which samples taken at different times from the same patient must be assayed for the analyte of interest, such as fecal occult blood. The presence of fecal occult blood is frequently determined by means of a series of stool samples taken once a day or at other intervals for a prescribed period. Alternatively, one or more of the assays can be used for controls or reference standards.

2. Multiplex Device with Collapsible Well

In yet another variation of the multiplex device, at least one sample preparation zone can comprise a collapsible well, to which an extraction swab or other sample-containing device can be added.

This variation of the multiplex device is shown in FIG. 11A. The device 440 has a first opposable component 442 and a second opposable component 444. The second opposable component 444 is hingedly attached to the first opposable component 442 by a hinge 446. The first opposable component 442 has a control well 448 and a collapsible sample well 450, i.e., made of a sponge-like material. The second opposable component 444 has a plurality of laterally separated chromatographic media 452, in this example, two, each with a first end 454 and a second end 456. Each of the chromatographic media 452 has a detection zone 458 and a control zone 460. Attached to the second opposable component 444 is a plurality of conductive barriers 462, one for each chromatographic medium 452.

The first opposable component has an aperture 464 for viewing of a portion of each of the chromatographic media 452, including the detection zone 458 and the control zone 460. The first and second opposable components 442 and 444 include engagers 466 and 468 and a gasket 470. When the first opposable component 442 and the second opposable component 444 are opposed, samples in the control well 448 and the collapsible sample well 450 are applied to the corresponding chromatographic media 452 through the conductive barriers 462 for chromatography.

If a collapsible well is included, the first opposable component can include, in place of the gasket 470, hingedly foldable wings 472 that fold over the second opposable component when the first opposable component and second opposable component are brought into opposition. This version of a multiplex assay device according to the present invention is shown in FIG. 11B.

In this and other embodiments of the present invention that are adapted to the use of a swab, the device typically can accommodate a wide variation in the quantity of liquid applied to the swab, so that oversaturation of the swab is not deleterious. The device is designed so that liquid that migrates into the perimeter area surrounding the swab does not interfere with the operation of the device.

3. Multiplex Device Adapted to Receive Test Card

Yet another variation of the multiplex device is particularly useful for determination of hemoglobin in fecal occult blood. This device is adapted to receive a test card that includes several dried fecal samples, typically taken on consecutive days.

This variation is shown in FIG. 12. The assay device 480 has a first opposable component 482 and a second opposable component 484. The second opposable component 484 is hingedly attached to the first opposable component 482 by a hinge 486. The first opposable component 482 includes a plurality of laterally separated reagent pads 488, i.e., applicators. Preferably, each applicator 488 contains labeled specific binding partner for the analyte in resolubilizable form.

The second opposable component 484 includes a chromatographic medium 490 for each reagent pad 488 on the first opposable component 482. The chromatographic media 490 are laterally separated. Each of the chromatographic media 490 has a first end 492 and a second end 494, and comprises a detection zone 496 and a control zone 498. The first end 492 of each chromatographic medium 490 is in operable contact with a conductor 500, and the second end 494 of each chromatographic medium 490 is in operable contact with an absorber 502. There is a separate conductor 500 and absorber 502 for each chromatographic medium 490. The second opposable component 484 is adapted to receive a test card 504 containing a plurality of dried specimens 506 positioned so that they are in operable contact with each conductor 500, such as by a recess 508 in the second opposable component 484.

Attached to the second opposable component 484 is a plurality of conductive barriers 510, one for each chromatographic medium 490.

The second opposable component 482 contains a plurality of apertures 512, one for each chromatographic medium 488, for viewing of each chromatographic medium 488. The first and second opposable components 482 and 484 each includes engagers 514 and 516 and a gasket 518 to retain samples and reagents.

In use, a buffer or other liquid is applied to each applicator 488 to reconstitute the labeled specific binding partner. Bringing the first and second opposable components 482 and 484 into opposition causes each of the applicators 488 to be applied to the corresponding dried specimen 506 so that the contents of each dried specimen 506 and each applicator 488 are applied to each conductive barrier 510, and then to the conductors 500, and thus to the first end 492 of each chromatographic medium 490. The test card 504 holds each of the specimens 506 in position so that they can receive the contents of the applicators 488, and so that analyte in the specimens 506 is extracted, reacts with the labeled specific binding partner, and is applied to the conductive barriers 510 and then to the conductors 500.

Still other variations of test devices according to the present invention are possible. For example, any of the two-component devices described can have a cover hingedly attached to one of the opposable components. This cover can have an aperture cut therein to allow viewing of at least a portion of the chromatographic medium.

II. ANALYTES AND ANTIBODIES FOR USE WITH ASSAY DEVICES

The analytes suitable for detection with an assay device according to the present invention include antigens, haptens, and antibodies. Antigens detectable with the device include hemoglobin, Streptococcus A and B antigens, antigens specific for the protozoan parasite Giardia, and viral antigens, including antigens specific for HIV and the Australia antigen specific for hepatitis. Antibodies that can be assayed include antibodies to bacteria such as *Helicobacter pylori* and to viruses, including HIV. Haptens detectable include haptens to which antibodies of sufficient specificity can be prepared.

Two antigens for which devices according to the present invention are particularly suitable are human hemoglobin and Streptococcus A antigen. The detection of human hemoglobin is clinically significant, because the presence of human hemoglobin in fecal material is a marker of intestinal or rectal bleeding, which is indicative of the presence of cancer in the gastrointestinal system or other pathogenic conditions. The detection of Streptococcus A antigen is also clinically significant, because streptococcal infections are fast-moving and can be life-threatening.

If the analyte is an antigen or a hapten and a sandwich procedure is used, the first and second specific binding partners are preferably antibodies. In many applications, it is preferable that the first and second specific binding partners are antibodies to different epitopes on the analyte, but this is not required. The antibodies can be polyclonal or monoclonal, and can be IgG, IgM or IgA. In many applications, polyclonal antibodies are preferred, as their natural variability may allow more accurate detection in systems where antigenic polymorphisms exist or may exist.

When the analyte is a hapten and a sandwich assay procedure is used, it is strongly preferred that the first and second specific binding partners be antibodies to different epitopes; otherwise, there may be an undesirable competition reaction set up that may interfere with binding of the complex of the labeled specific binding partner and the analyte to the immobilized second specific binding partner. It is recognized that not all haptens are large enough to accommodate more than one epitope; however, some haptens, though not large enough to induce antigen formation efficiently when injected by themselves, are nevertheless large enough that they possess more than one epitope. In cases where antibodies to more than one epitope of a hapten cannot be obtained, competitive assay procedures are generally preferred.

Where the analyte is an antibody and a sandwich assay procedure is used, the first specific binding partner is typically a labeled antibody that binds to the analyte on the basis of species, class, or subclass (isotype) specificity. It is highly preferred that the first specific binding partner to an antibody analyte binds to the constant region of the antibody analyte, in order to prevent interference. When the analyte is antibody, the second specific binding partner is preferably an antigen or hapten for which the antibody analyte is specific.

In some applications, it is desirable to employ indirect labeling. For example, in testing for Giardia antigen, an IgM antibody can be used that may be difficult to label directly. In that case, a secondary specific binding partner specific for the mobile first specific binding partner can be labeled. Typically, the labeled secondary specific binding partner binds to the antibody that is the first specific binding partner on the basis of species, class, or subclass specificity.

As an alternative to the use of a secondary specific binding partner, the first specific binding partner can be conjugated to biotin and an avidin-conjugated label can be used.

These relationships between analytes, specific binding partners, and labels for sandwich immunoassays are summarized in Table I below.

TABLE I

SCHEMES OF BINDING FOR SANDWICH IMMUNOASSAYS

| ANA-LYTE | 1ST SBP (MOBILE) | 2ND SBP (FIXED) | SECON-DARY SBP | COMPLEX FORMED |
|---|---|---|---|---|
| Ag | $Ab_1$* | $Ab_2$ | — | $Ab_2$-Ag-$Ab_1$* |
| H | $Ab_1$* | $Ab_2$ | — | $Ab_2$-H-$Ab_1$*[(1)] |
| Ab | $Ab_c$* | Ag | — | Ag-Ab-$Ab_c$* |
| Ag | $Ab_1$ | $Ab_2$ | $Ab_c$* | $Ab_2$-Ag-$Ab_1$-$Ab_c$* |
| Ab | $Ab_{c1}$ | Ag | $Ab_{c2}$* | Ag-Ab-$Ab_{c1}$-$Ab_{c2}$* |

TABLE I-continued

SCHEMES OF BINDING FOR SANDWICH IMMUNOASSAYS

| ANA-LYTE | 1ST SBP (MOBILE) | 2ND SBP (FIXED) | SECON-DARY SBP | COMPLEX FORMED |
|---|---|---|---|---|
| Ag | $Ab_1$-Bi | $Ab_2$ | Av-L | $Ab_2$-Ag-$Ab_1$-Bi-Ay-L |

Ag = Antigen
H = Hapten
Ab = Antibody
$Ab_1$ = 1st Antibody
$Ab_2$ = 2nd Antibody
$Ab_c$, $Ab_{c1}$, $Ab_{c2}$ = Antibody specific for another antibody
Bi = Biotin
Av = Avidin
L = Label
*Indicates labeled component
[(1)]$Ab_2$ and $Ab_1$* preferred to bind to different epitopes; not all haptens possess such different epitopes.

III. TEST KITS

Another aspect of the present invention is test kits that can be used to detect particular analytes. A test kit comprises, in separate containers:

(1) a chromatographic assay device according to the present invention;

(2) any necessary reagents required to treat or extract the sample; and (3) optionally, if the assay device does not incorporate a labeled specific binding partner to the analyte in a form that can be resolubilized, the required specific binding partner.

The components required in (2) and (3) are packaged separately and can be in liquid or solid form (freeze-dried, crystallized, precipitated, or aggregated). If the latter, they are resolubilized by the user, typically with distilled or purified water, with physiological saline, or a buffer solution.

The reagents required to treat or extract the sample are those described above. In some cases, such reagents can interact with a reagent incorporated in the device in resolubilizable form. An example is the generation of nitrous acid by the reaction of sodium nitrite with acetic acid or another weak acid.

In some cases, test kits can also include a reconstitution fluid for a reagent present on the device in resolubilizable form, either a specific binding partner or an analyte analogue. Specific examples are disclosed above, with the disclosure of the operation of each type of device.

The invention is illustrated by the following Examples. The Examples are for illustrative purposes only and are not to be construed as limiting the scope of the invention in any manner.

EXAMPLES

Example 1

Construction of Device for Detecting Streptococcal Antigen

A device was constructed for detecting Streptococcus A antigen using labeled antibody to Streptococcus A antigen. The device was constructed essentially as depicted in FIG. 13.

FIG. 13 shows a chromatographic assay device 540 according to the present invention with a first opposable component 542, and a second opposable component 544 hingedly attached to the first opposable component 542 by a hinge 545. The first opposable component 542 includes a chromatographic medium 546 with first and second ends 548 and 550, a detection zone 552, and a control zone 554. The first opposable component 542 also includes a zone of resolubilizable anti-Streptococcus A antibody 556 (detector application pad) adjacent to the first end 458 of the chromatographic medium 546. The first opposable component also includes an absorber 558 adjacent to the second end 550 of the chromatographic medium 546. Attached to the first opposable component 542 is a conductive barrier 560. The second opposable component 544 includes a well 562 that can receive a throat swab. The well 562 is covered with an impermeable barrier 564 that has two apertures, one at each end of the well, a first aperture 566 for insertion of the swab and a second aperture 568 for application of the extracted sample to the conductive barrier 560. The first opposable component 542 contains a window 570.

The opposable components were made of a hard, impervious plastic such as polycarbonate. The first and second opposable components each were about 3" in length; the first opposable component was about 2.25" in width, while the second opposable component was each about 2.375" in width. The second opposable component was lined with a foam rubber receptacle, into which a teardrop-shaped well was cut to accept a swab or other sampling device.

The chromatographic medium was a nitrocellulose strip of 8 μm pore size and 0.5" in length, (MSI, Westborough, Mass.), affixed to the plastic backing by means of double-sided tape (3M, Minneapolis, Minn.). The conductive barrier and absorber were cellulose strips (Ahlstrom Filtration, Holly Springs, Pa.), $^{17}/_{32}$" in length for the absorber, which was Ahlstrom Grade 939, and 0.25" in length for the conductive barrier, which was Ahlstrom Grade 1281. The detector application pad was also Ahlstrom Grade 1281, and was 0.375" wide. The chromatographic medium overlapped slightly at its second end with the absorber.

The required reagents were first incorporated in the chromatographic medium and the zone of resolubilizable antibody, after which the device was assembled using double-sided tape to hold the components to the backing.

The detection zone comprised rabbit anti-Streptococcus A antibody at 2 mg/ml in 0.001 mole/l phosphate buffered saline, pH 7.2. The control zone comprised goat anti-rabbit IgG at a similar concentration in the same buffer. The antibody solutions were applied to the appropriate regions of the chromatographic medium and dried at 100° F. in a low humidity environment. The chromatographic medium was wet in excess blocking solution (Blocking Reagent for ELISA, Boehringer Mannheim, Mannheim, Germany, diluted 1:10 with distilled water containing 0.2% Tween 20) and again dried at 100° F.

The detector application pad contained rabbit anti-Streptococcus antibody labeled with 40-nm colloidal gold particles. To apply the labeled antibody to the detector application pad, the labeled antibody was diluted 1:1.5 with DBN (1.5 mole/l Tris-HCl, pH 7.4, 1% (v/v) Tween 20, 0.4% (v/v) Brij 35, 0.02% (w/v) sodium azide, 3 mg/ml rabbit IgG). Per test, 15 μl of diluted labeled antibody was added to the detector application pad. The detector application pad was dried for 30 minutes at 100° F.

Example 2

Detection of Streptococcal Antigen Using Device of Example 1

The device of Example 1 was used to detect Streptococcus A antigen. A woven dacron swab to which varying quantities of Streptococcus type A bacteria had been added was inserted into the sample well. Three drops of Extraction Reagent A (0.25% acetic acid, 5% Tween 20), and three drops of Extraction Reagent B (2 mole/l sodium nitrite, 5% Tween 20) were added to the swab, mixed by gently rotating the swab, and incubated for one minute. The device was then closed, so that the first and second opposable components were brought into contact. The result was read after an incubation period of from 2 minutes to 5 minutes. The development of a pink-red band in the detection zone of the chromatographic medium indicated the detection of Streptococcus A antigen.

The device of Example 1 could detect $1\times10^5$ Streptococcus A organisms after a 2-minute incubation, and could detect $5\times10^4$ Streptococcus A organisms after a 5-minute incubation. For a comparison, the Concise™ immunoassay of Hybritech (La Jolla, Calif.) could detect $1\times10^5$ Streptococcus A organisms only after a 5-minute incubation, and could not detect $5\times10^4$ Streptococcus A organisms even after a 20-minute incubation. Similarly, the Smart™ immunoassay of New Horizons could detect $1\times10^5$ Streptococcus A organisms only after a 7-minute incubation, and gave an equivocal result with $5\times10^4$ Streptococcus A organisms after a 7-minute incubation.

Example 3

Device for Detecting Hemoglobin in Fecal Occult Blood

An assay device for the detection of hemoglobin in fecal occult blood was constructed according to FIGS. 4A and 4B, with details of materials and construction as in Example 1. A labeled specific binding partner was applied to the sample application pad in resolubilizable form. The labeled specific binding partner was goat anti-human antibody labeled with colloidal gold. A fecal sample of 60 μl was applied to the sample application pad and allowed to mix with conjugate. The device was closed and the combination of the fecal sample and reconstituted antibody contacted the conductor and moves through the chromatographic medium. Chromatography was allowed to proceed for a period of about 1 minute to about 5 minutes. The chromatographic medium contained a detection zone of immobilized anti-human Hb antibody, and a control zone of immobilized rabbit anti-goat IgG antibody.

Color appearing at both the detection zone and the control zone indicates a positive result, i.e., the presence of occult blood in the fecal sample. Color appearing at the control zone, but not at the detection zone, indicates the absence of occult blood and the correct performance of the test.

This device is capable of detecting hemoglobin in fecal occult blood in a concentration range of from about 0.2 ml blood/100 g feces to about 17 ml blood/100 g feces. This device is free from interference caused by peroxidase and dietary (non-human) hemoglobin.

ADVANTAGES OF THE INVENTION

Chromatographic assay devices according to the present invention provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, each as those containing HIV or hepatitis virus.

Another advantage of assay devices according to the present invention lies in the ability of the devices to use pressure to drive fluid from one opposable component to another and through the chromatographic medium and to control the pressure applied so that it is optimum for each assay to be carried out. This accelerates the assay process and allows the performance of operations such as extraction within the assay device. It also reduces the dead volumes of reagents remaining in components, allowing the use of smaller samples and smaller quantities of expensive or hard-to-purify reagents such as labeled antibodies.

Yet another advantage of assay devices according to the present invention results from the use of the conductive barrier to control flow and prevent irregular flow or high local concentrations of a reactant in a specific binding reaction. This provides greater reproducibility and reliability in the performance of assays using assay devices according to the present invention.

Additionally, chromatographic assay devices according to the present invention allow the rapid and accurate detection of clinically important analytes, such as Streptococcus A and B antigen, hemoglobin for the determination of fecal occult blood, and antibody to *Helicobacter pylori,* as well as clinically important haptens. The construction of the devices allows more even application of the samples to the chromatographic medium, and reduces interference that might otherwise be introduced by particulates or colored samples. The use of colloidal metal labels in a resolubilizable form provides extremely rapid kinetics of labeling and allows substantially complete formation of binary analyte-label complexes before the sample is applied to the chromatographic medium. This aids in the separation of contaminants and improves the performance of the assay. Additionally, the construction and arrangement of the housing of the device aids in the performance of the assay by assuring the withdrawal of excess immunoglobulin-containing sample that could otherwise create interference.

Extraction of biological samples such as blood, sputum, or feces can be performed directly in the devices, reducing the quantity of contaminated material that must be disposed and reducing the likelihood of accidental infection of physicians, technicians, or the public by such contaminated material. Additionally, the devices are capable of performing bidirectional chromatography to further increase accuracy and reduce interference. Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two- or three-component devices that operate by the basic principles described herein and utilize any of: (a) in situ extraction of samples; (b) resolubilization of a labeled specific binding partner and rapid binding to analyte; and (c) arrangement of the chromatographic medium and absorber to remove excess sample that could otherwise create interference. These versions include assay devices adapted for competitive immunoassays as well as sandwich immunoassays, in various arrangements. In particular, devices according to the present invention can be adapted to make use of radial or circumferential flow through a chromatographic medium rather than linear flow. The present invention further encompasses variations in which the two or three components of the device are not held in a permanently fixed arrangement, but can be separated and brought together to perform the assay, such as by electrical or magnetic forces or by using a separable fastener such as a hook-and-eye fabric, for example Velcro™. Therefore, the scope of the invention is determined by the following claims.

I claim:

1. A chromatographic assay device for detection or determination of at least one analyte comprising:
   (a) a first opposable component including a plurality of laterally separated reagent pads;
   (b) a second opposable component for receiving a test card containing a plurality of dried specimens, the second opposable component including:
      (i) a chromatographic medium for each sample preparation means on the first opposable component, the chromatographic media being laterally separated, each chromatographic medium having a first and a second end and a detection zone with an immobilized first specific binding partner for an analyte;
      (ii) a conducting means in operable contact with the first end of each chromatographic medium and in operable contact with each dried specimen of the test card when the test card is inserted into the second opposable component; and
      (iii) an absorbing means in operable contact with the second end of each chromatographic medium; and
   (c) a plurality of conductive barriers each attached to the second opposable component, one for each chromatographic medium wherein the first and second opposable components can be brought into opposition so as to cause each reagent pad to be applied to the corresponding dried specimen through the corresponding conductive barrier for detection or determination of the at least one analyte at at least one detection zone of at least one chromatographic medium.

2. The chromatographic assay device of claim 1 wherein each reagent pad includes a second specific binding partner for the analyte labeled with a detectable label in a form that can be resolubilized by the addition of an aqueous reagent to the reagent pad.

3. The chromatographic assay device of claim 2 wherein the analyte is human hemoglobin and the second specific binding partner is an anti-human hemoglobin antibody.

4. A method for detecting or determining an analyte in a test sample, comprising the steps of:
   (a) placing a test card containing at least one dried specimen in contact with a first opposable component of the chromatographic assay device of claim 2;
   (b) adding an aqueous reagent to each reagent pad of the second opposable component corresponding to a dried specimen;
   (c) placing the first and second opposable components into opposition, thereby applying the sample and the contents of the reagent pad to at least one of the chromatographic media through the corresponding conductive barrier;
   (d) allowing the sample and the contents of the reagent pad to move through at least a portion of at least one of the chromatographic media, the portion including the detection zone, so that the label of the second specific binding partner gives a detectable indication of the presence or quantity of the analyte; and (e) observing or measuring the label in at least one of the chromatographic media at the detection zone in order to detect or determine the analyte.

5. The method of claim 4 wherein the analyte is hemoglobin.

6. A test kit for the detection and/or determination of an analyte comprising, separately packaged:

(a) the chromatographic assay device of claim 1;

(b) a test card for insertion into the chromatographic assay device that can contain a plurality of dried specimens; and (c) an extraction reagent for the analyte to be assayed, the extraction reagent to be applied to the test card.

* * * * *